(12) United States Patent
Shimizu

(10) Patent No.: US 11,261,149 B2
(45) Date of Patent: Mar. 1, 2022

(54) METHOD FOR PRODUCING ACETIC ACID

(71) Applicant: DAICEL CORPORATION, Osaka (JP)

(72) Inventor: Masahiko Shimizu, Himeji (JP)

(73) Assignee: DAICEL CORPORATION, Osaka (JP)

( * ) Notice: Subject to any disclaimer, the term of this patent is extended or adjusted under 35 U.S.C. 154(b) by 434 days.

(21) Appl. No.: 16/482,675

(22) PCT Filed: Jul. 2, 2018

(86) PCT No.: PCT/JP2018/025074
§ 371 (c)(1),
(2) Date: Jul. 31, 2019

(87) PCT Pub. No.: WO2020/008503
PCT Pub. Date: Jan. 9, 2020

(65) Prior Publication Data
US 2021/0355062 A1  Nov. 18, 2021

(51) Int. Cl.
*C07C 51/12* (2006.01)
*C07C 51/44* (2006.01)
(Continued)

(52) U.S. Cl.
CPC .......... *C07C 51/12* (2013.01); *B01D 53/1418* (2013.01); *C07C 51/44* (2013.01);
(Continued)

(58) Field of Classification Search
CPC ........ C07C 51/12; C07C 51/42; C07C 51/44; C07C 53/08; C07C 2523/46; B01D 1/0064; B01D 53/1418; B01D 53/1493
See application file for complete search history.

(56) References Cited

U.S. PATENT DOCUMENTS 7,473,800 B2 * 1/2009 Hosono ............... B01J 31/181
562/519
9,458,077 B2  10/2016 Shaver et al.
(Continued)

FOREIGN PATENT DOCUMENTS

| JP | 2016-121126 A | 7/2016 |
|---|---|---|
| WO | WO 2015/193328 A1 | 12/2015 |
| WO | WO 2018/078924 A1 | 5/2018 |

OTHER PUBLICATIONS

Office Action and Examination Report dated Oct. 8, 2020, in counterpart GCC Patent Application No. 2019/37833.
(Continued)

*Primary Examiner* — Yate' K Cutliff
(74) *Attorney, Agent, or Firm* — Birch, Stewart, Kolasch & Birch, LLP

(57) ABSTRACT

Provided is an acetic acid production method including an absorption step that enables efficient and energy-saving separation of methyl iodide in a downstream step, when provided, of separating methyl iodide from a solution after the absorption of methyl iodide. The acetic acid production method according to the present invention includes an absorption step in an acetic acid production process. In the absorption step, at least a portion of offgases formed in the process is fed to an absorption column, is brought into contact with an absorbent including an organic acid having a higher boiling point as compared with acetic acid to allow the absorbent to absorb an iodine compound from the offgas, and a gas having a lower iodine compound concentration as compared with the offgas, and a solution containing the absorbent and the iodine compound are thereby to be separated.

20 Claims, 10 Drawing Sheets

(51) Int. Cl.
   *B01D 53/14* (2006.01)
   *C07C 53/08* (2006.01)
   *C07C 51/42* (2006.01)

(52) U.S. Cl.
   CPC .............. *C07C 51/42* (2013.01); *C07C 53/08* (2013.01); *C07C 2523/46* (2013.01)

(56) References Cited

U.S. PATENT DOCUMENTS

| | | |
|---|---|---|
| 2009/0270651 A1 | 10/2009 | Zinobile et al. |
| 2016/0137574 A1 | 5/2016 | Shaver et al. |
| 2020/0140366 A1* | 5/2020 | Shimizu ................ C07C 51/445 |

OTHER PUBLICATIONS

English translation of International Search Report for PCT/JP2018/025074(PCT/ISA/210) dated Jul. 31, 2018,.
English translation of Written Opinion of the International Searching Authority for PCT/JP2016/025074 dated Nov. 15, 2019.
European Office Action dated Aug. 14, 2020 issued for the European Patent Application No. 18905891.0.
International Search Report for PCT/JP2018/025074 (PCT/ISA/210) dated Jul. 31, 2018.
Written Opinion of the International Searching Authority for PCT/JP2018/025074 (PCT/ISA/237) dated Jul. 31, 2018.
Extended European Search Report dated Apr. 14, 2020, in European Patent Application No. 18905891.0.

* cited by examiner

[FIG. 1]
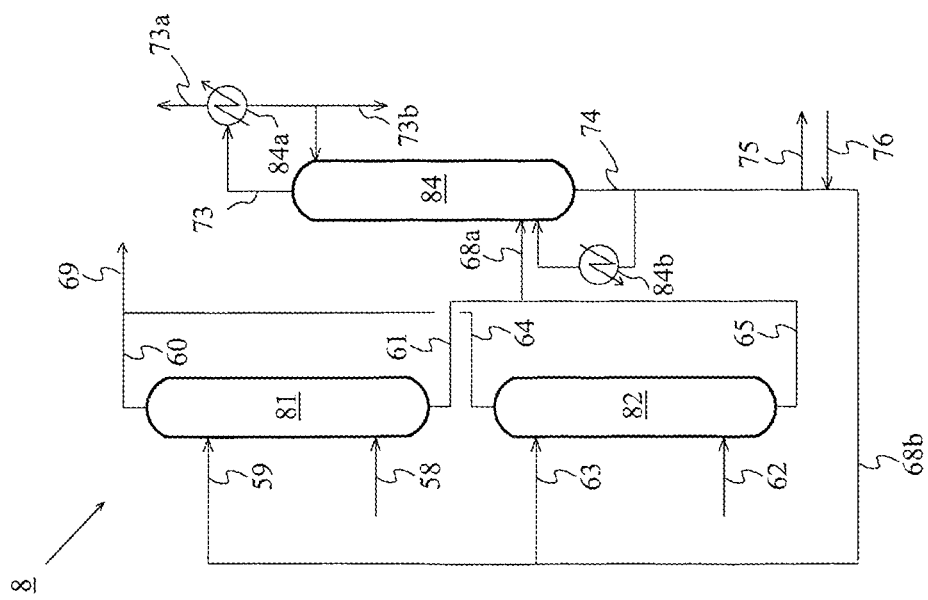
[FIG. 2]
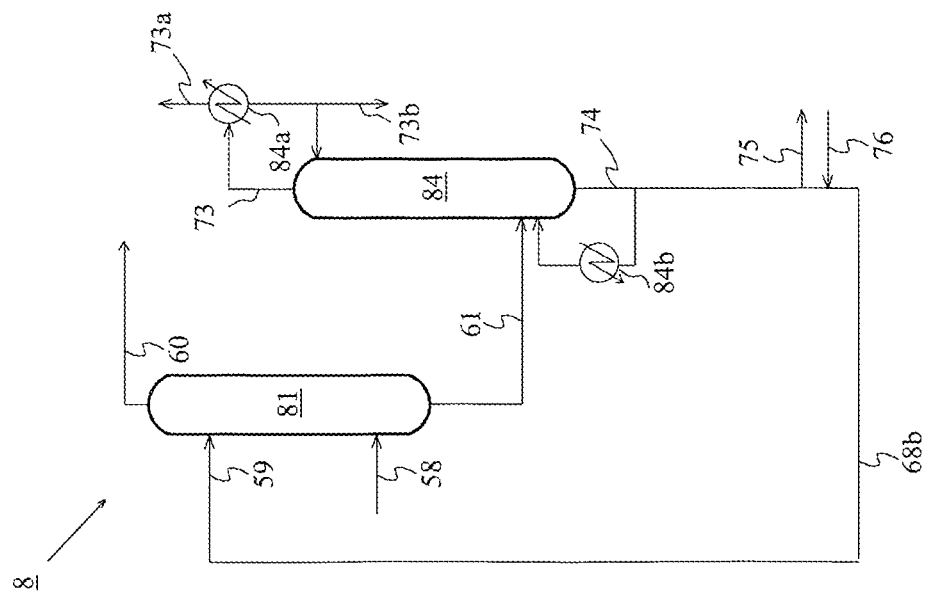

[FIG. 3]
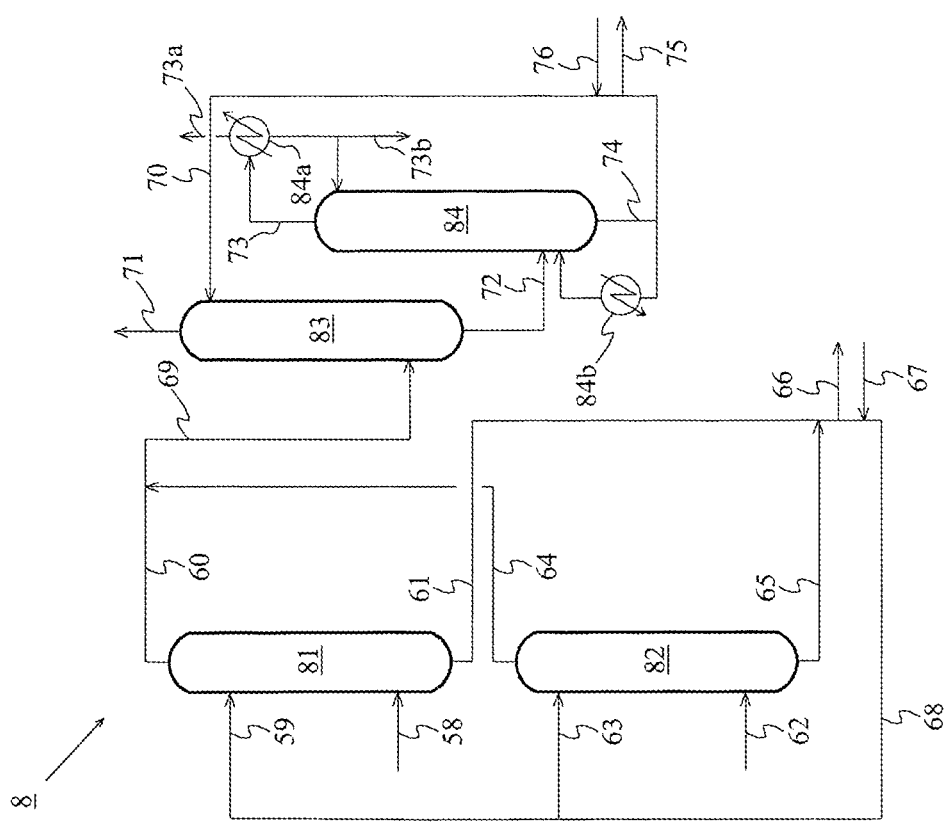

[FIG. 4]
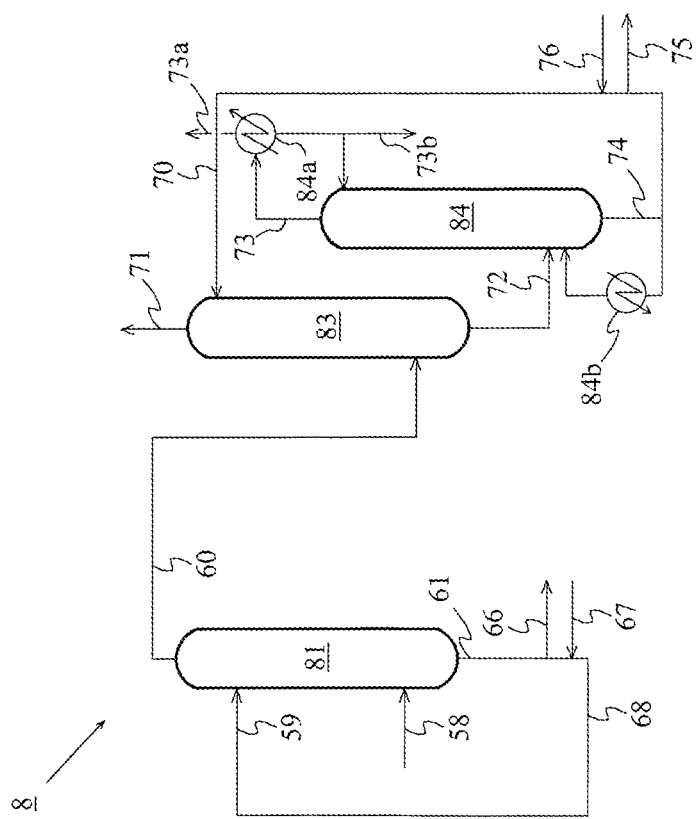

[FIG. 5]
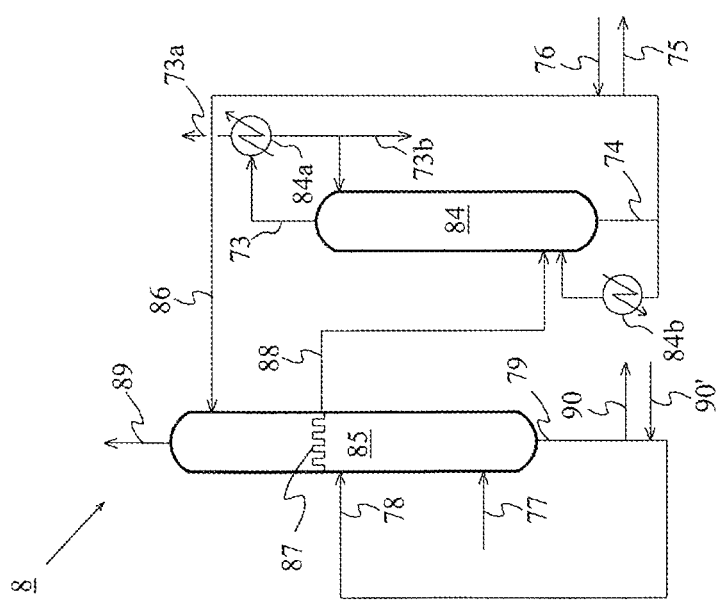

[FIG. 6]
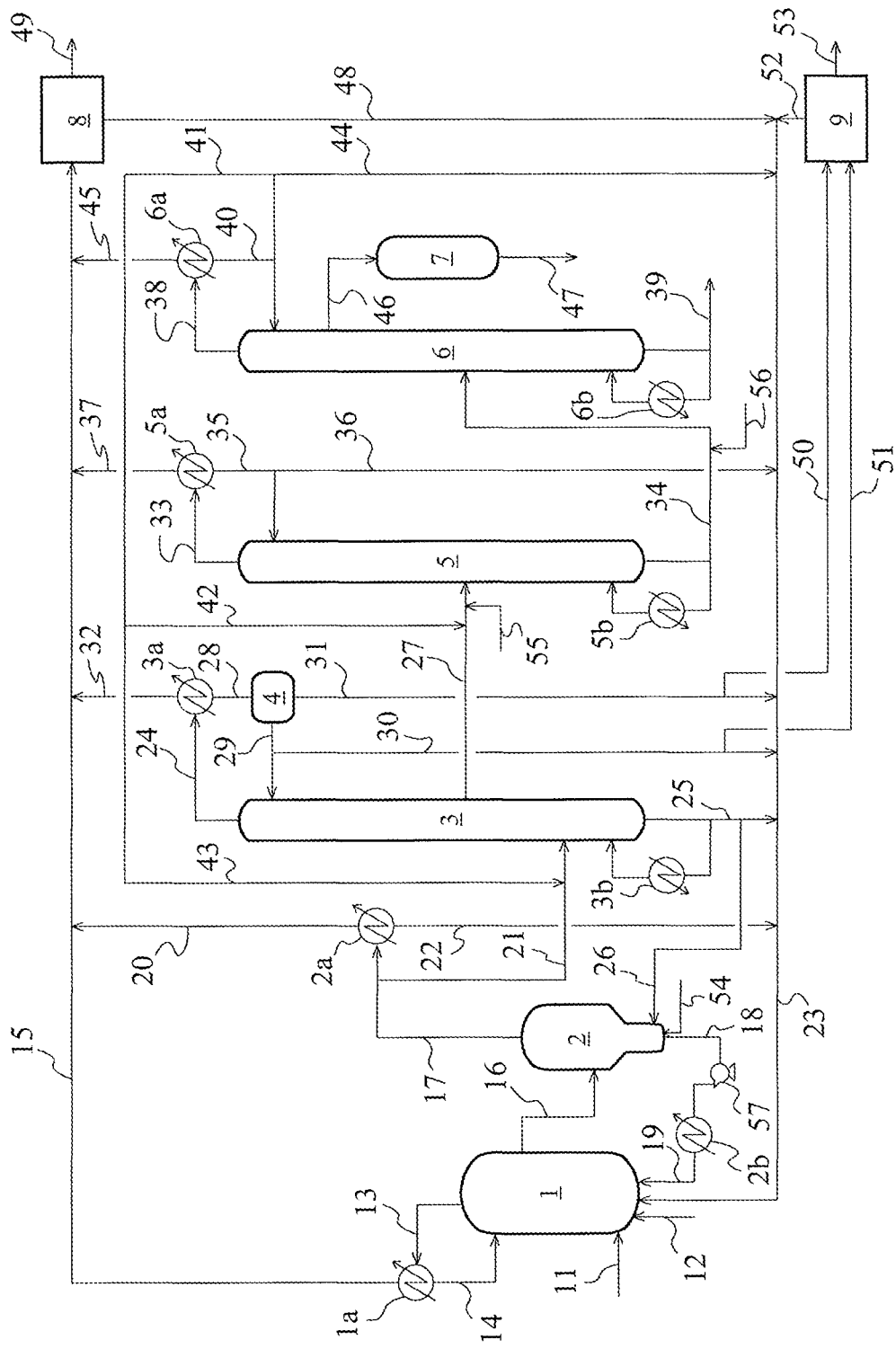

[FIG. 7]
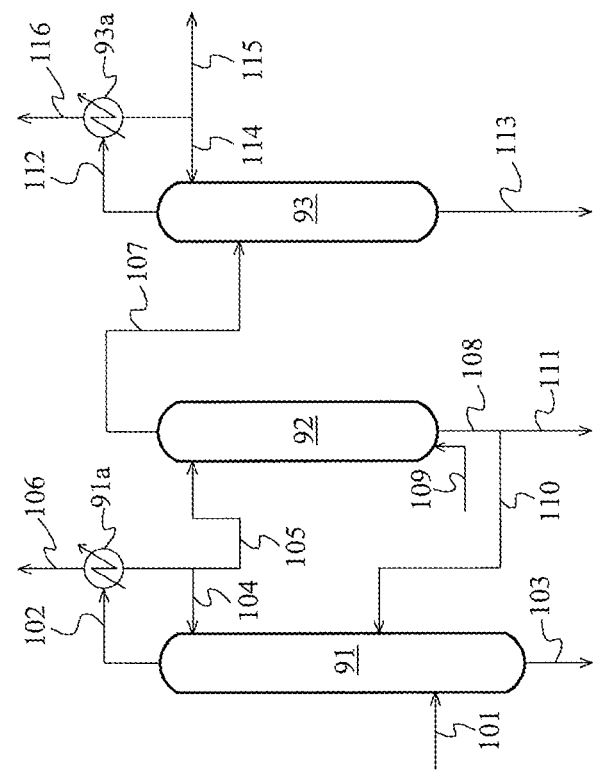

[FIG. 8]
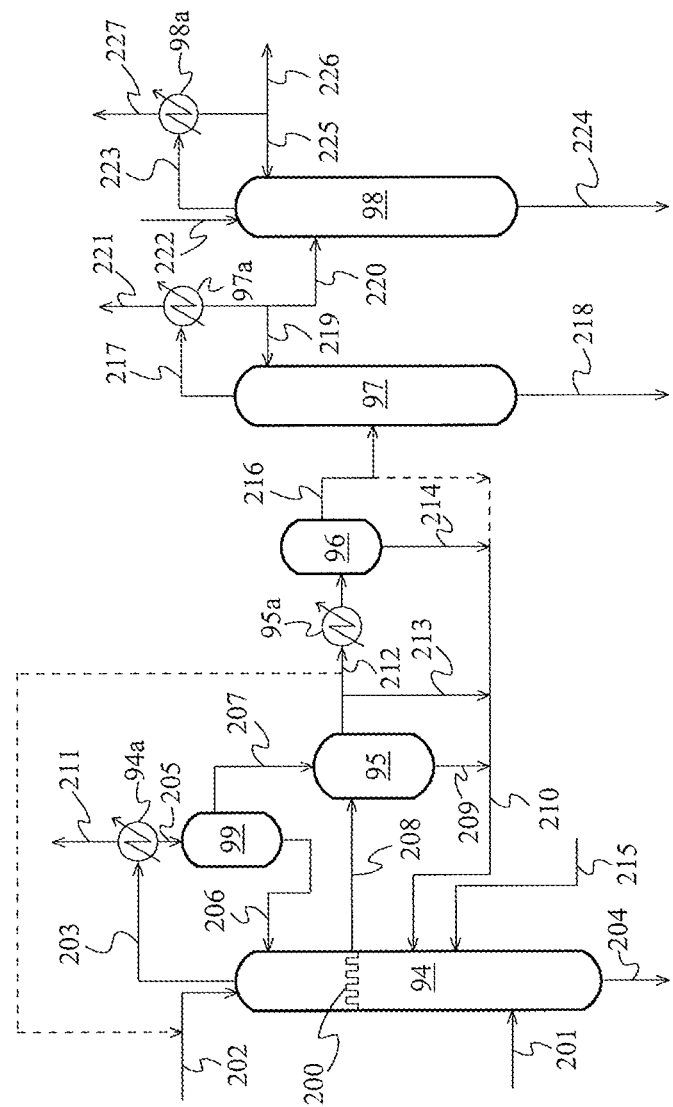

[FIG. 9]
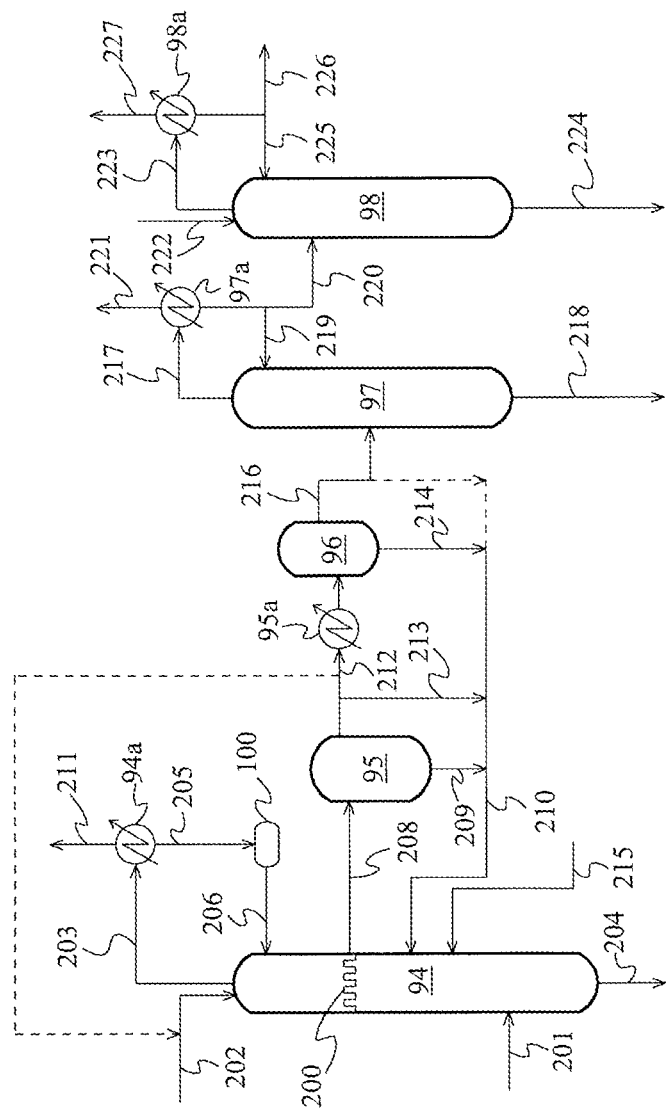

[FIG 10]
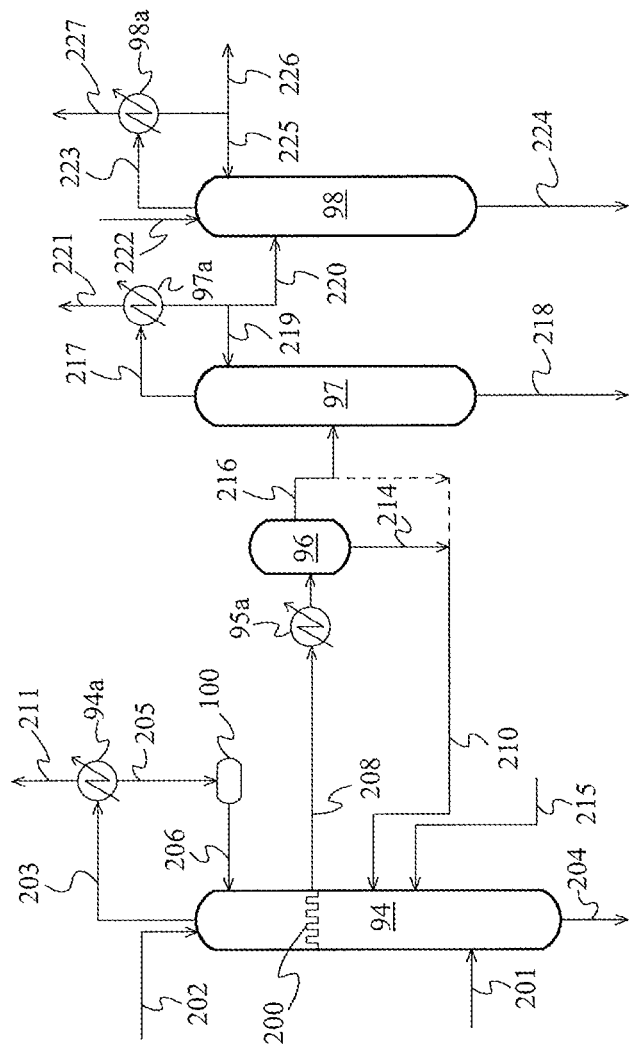

[FIG. 11]
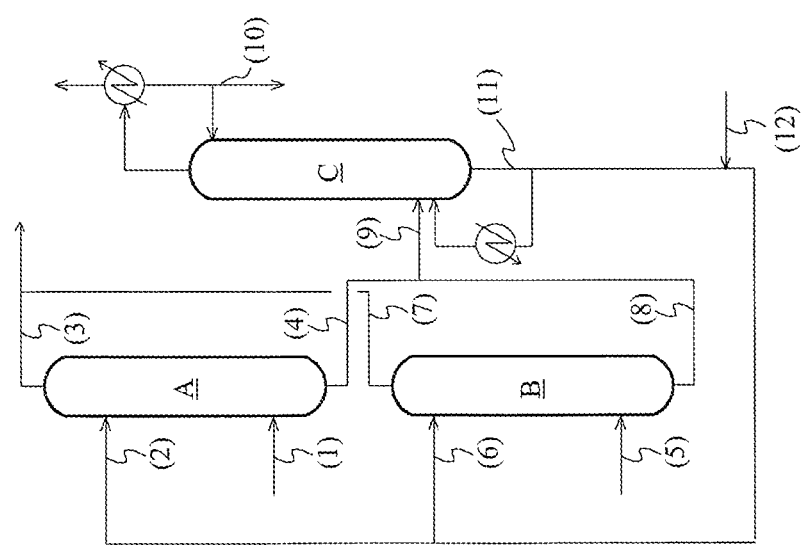

METHOD FOR PRODUCING ACETIC ACID

TECHNICAL FIELD

The present invention relates to methods for producing acetic acid.

BACKGROUND ART

A methanol carbonylation process (methanol-acetic acid process) is known as a method for industrially producing acetic acid. In this process, for example, methanol is reacted with carbon monoxide in the presence of a catalyst in a reactor to form acetic acid, the resulting reaction mixture is subjected to evaporation in an evaporator to give a vapor phase, the vapor phase is purified through a light ends column and subsequently through a dehydration column to give an acetic acid product, or further purified through a heavy ends column subsequent to the dehydration column, and, further, through a product column to give an acetic acid product.

In the acetic acid production process as above, an offgas from a process typically using a reaction system or a purification system includes useful components (such as methyl iodide, water, methyl acetate, and acetic acid). Before discarding of the offgas, the useful components are recovered from the offgas typically by absorption treatment with an absorbing solvent in a scrubbing system.

Patent Literature (PTL) 1 discloses an acetic acid production method in which a specific process stream is brought into contact with a first absorbent selected from the group consisting of acetic acid, methanol, and methyl acetate, or further brought into contact with a second absorbent including at least one of methanol and methyl acetate.

CITATION LIST

Patent Literature

PTL 1: Japanese Unexamined Patent Application Publication (JP-A) No. 2016-121126

SUMMARY OF INVENTION

Technical Problem

The resulting solution after absorption of such useful components is then fed to a distillation column and is separated, by distillation, into the useful components and the absorbing solvent (absorbent). By the distillation, the useful components such as methyl iodide are generally concentrated in an overhead stream from the distillation column, and the concentrated methyl iodide can be recycled to the reactor and reused in the reaction step.

However, disadvantageously, the method disclosed in PTL 1, when employing acetic acid, methanol, or methyl acetate as the absorbing solvent, is susceptible to improvements in separation efficiency in separation of the solution after absorbing useful components by distillation, because the absorbing solvent and methyl iodide have a relatively small difference in boiling point from each other. The solution after absorbing useful components, when subjected to distillation using a distillation column operated at a higher reflux ratio, is more readily separated into the useful components and the absorbing solvent. However, this requires a larger amount of steam to be used in heating of the distillation column operated at such a higher reflux ratio, and tends to cause poor energy saving.

Accordingly, the present invention has an object to provide an acetic acid production method including such an absorption step that enables efficient and energy-saving separation of methyl iodide in a downstream step, when provided, of separating methyl iodide from a solution that has absorbed methyl iodide.

Solution to Problem

To achieve the object, the inventor of the present invention made intensive investigations while focusing on the difference in boiling point between methyl iodide and an absorbing solvent, and on the relationship among the reflux ratio, separation efficiency, and steam amount in a stripping step of separating useful components. As a result, the inventor found that the use of, as the absorbing solvent, a solvent having a large difference in boiling point from methyl iodide enables efficient separation of methyl iodide while saving the steam amount in the subsequent (downstream) distillation step. The present invention has been made on the basis of these findings and further investigations.

Specifically, the present invention provides, in one aspect, an acetic acid production method that includes an absorption step. In the absorption step, at least a portion of offgases formed in an acetic acid production process is fed to an absorption column, the fed offgas is brought in contact with an absorbent including an organic acid having a higher boiling point as compared with acetic acid to allow the absorbent to absorb an iodine compound from the offgas, and whereby the a gas having a lower iodine compound concentration as compared with the offgas, and a solution containing the absorbent and the iodine compound are separated.

The present invention also provides, in another aspect, an acetic acid production method that includes a carbonylation step (reaction step) and a separation step, and may further include an acetaldehyde-removing system. This acetic acid production method includes an absorption step.

In the carbonylation step, methanol is reacted with carbon monoxide in the presence of a catalytic system, acetic acid, methyl acetate, and water in a reactor to form acetic acid, where the catalytic system includes a metal catalyst and methyl iodide.

In the separation step, a reaction mixture from the carbonylation step is separated, using at least one selected from evaporators and distillation columns, into a stream including the metal catalyst, an acetic acid stream rich in acetic acid, and a stream richer in light ends than the acetic acid stream.

In the acetaldehyde-removing system, acetaldehyde is separated, using a distillation column or columns, from at least a portion of a condensate resulting from condensation of the stream richer in light ends.

In the absorption step, at least one offgas is fed to an absorption column, where the at least one offgas is selected from the group consisting of an offgas from the reactor, an offgas from the evaporator(s), an offgas from the distillation column(s) in the separation step, and an offgas from the distillation column(s) in the acetaldehyde-removing system. The fed offgas in the absorption column is brought into contact with an absorbent including an organic acid having a higher boiling point as compared with acetic acid to allow the absorbent to absorb an iodine compound from the offgas. A gas having a lower iodine compound concentration as compared with the offgas, and a solution containing the absorbent and the iodine compound are thereby to be separated.

The present invention also provides, in yet another aspect, an acetic acid production method that includes a carbonylation step (reaction step), an evaporation step, a light ends-removing step, and a dehydration step and may further include at least one of a heavy ends-removing step and an acetaldehyde-removing system. This acetic acid production method includes an absorption step.

In the carbonylation step, methanol is reacted with carbon monoxide in the presence of a catalytic system, acetic acid, methyl acetate, and water in a reactor to form acetic acid, where the catalytic system includes a metal catalyst and methyl iodide.

In the evaporation step, a reaction mixture from the carbonylation step is separated, by evaporation using an evaporator, into a vapor stream and a residue stream.

In the light ends-removing step, the vapor stream is separated, by distillation, into an overhead stream rich in light ends, and a first acetic acid stream rich in acetic acid.

In the dehydration step, the first acetic acid stream is separated, by distillation, into an overhead stream rich in water, and a second acetic acid stream richer in acetic acid than the first acetic acid stream.

In the heavy ends-removing step, the second acetic acid stream is separated, by distillation, into a bottom stream rich in heavy ends, and a third acetic acid stream richer in acetic acid than the acetic acid stream before being subjected to the distillation.

In the acetaldehyde-removing system, acetaldehyde is separated, using a distillation column or columns, from at least a portion of a condensate resulting from condensation of the overhead stream rich in light ends.

In the absorption step, at least one offgas is fed to an absorption column, where the at least one offgas is selected from the group consisting of an offgas from the reactor, an offgas from the evaporator, an offgas from a distillation column in the light ends-removing step, an offgas from a distillation column in the dehydration step, an offgas from a distillation column in the heavy ends-removing step, and an offgas from the distillation column(s) in the acetaldehyde-removing system. The fed offgas is brought into contact with an absorbent including an organic acid having a higher boiling point as compared with acetic acid to allow the absorbent to absorb an iodine compound from the offgas, and whereby a gas having a lower iodine compound concentration as compared with the offgas, and a solution containing the absorbent and the iodine compound are to be separated.

The organic acid in the absorbent is present preferably in a concentration of 10 ppm by mass or more.

The organic acid is preferably an organic acid having a boiling point of 120° C. to 300° C. at atmospheric pressure. The organic acid is preferably propionic acid.

The acetic acid production method may include a stripping step (desorption step). In the stripping step, the solution containing the absorbent and the iodine compound is separated, by distillation, into an overhead stream rich in methyl iodide, and a bottom stream rich in the organic acid.

The overhead stream rich in methyl iodide may be recycled to at least one step selected from the group consisting of a reaction step (carbonylation step), an evaporation step, and distillation steps.

A charge liquid to a distillation column in the stripping step preferably has a methyl iodide concentration of 100 ppm by mass or more.

The charge liquid to the distillation column in the stripping step preferably has a hydrogen iodide concentration of less than 1 mass percent.

The distillation column in the stripping step may be operated at a reflux ratio of 100 or less.

The bottom stream rich in the organic acid may be recycled to at least one of a reaction step and distillation steps.

Advantageous Effects of Invention

With the present invention, an organic acid having a higher boiling point as compared with acetic acid is used as an absorbent. This enables efficient and energy-saving separation of methyl iodide by distillation from a solution that includes absorbed methyl iodide. This is because the absorbent has a larger difference in boiling point from methyl iodide, as compared with acetic acid, methanol, or methyl acetate when used as the absorbent.

BRIEF DESCRIPTION OF DRAWINGS

FIG. 1 depicts a schematic flow chart illustrating a scrubbing system according to an embodiment;

FIG. 2 depicts a schematic flow chart illustrating a scrubbing system according to another embodiment;

FIG. 3 depicts a schematic flow chart illustrating a scrubbing system according to yet another embodiment;

FIG. 4 depicts a schematic flow chart illustrating a scrubbing system according to still another embodiment;

FIG. 5 depicts a schematic flow chart illustrating a scrubbing system according to another embodiment;

FIG. 6 is a production flow chart illustrating an acetic acid production system according to an embodiment;

FIG. 7 depicts a schematic flow chart illustrating an acetaldehyde-removing system according to an embodiment;

FIG. 8 depicts a schematic flow chart illustrating an acetaldehyde-removing system according to another embodiment;

FIG. 9 depicts a schematic flow chart illustrating an acetaldehyde-removing system according to yet another embodiment;

FIG. 10 depicts a schematic flow chart illustrating an acetaldehyde-removing system according to still another embodiment; and FIG. 11 depicts a schematic flow chart illustrating the structure of a scrubbing system used in examples and comparative examples.

DESCRIPTION OF EMBODIMENTS

The acetic acid production method according to an embodiment of the present invention includes an absorption step. By the absorption step, at least a portion of offgases formed in an acetic acid production process is fed to an absorption column, is brought into contact with an absorbent including an organic acid having a higher boiling point as compared with acetic acid, to allow the absorbent to absorb an iodine compound from the offgas, and whereby a gas having a lower iodine compound concentration as compared with the offgas, and a solution containing the absorbent and the iodine compound are to be separated. In the description, the absorption step is also referred to as an "absorption step according to the present invention".

In the acetic acid production method according to the present invention, at least a portion of all offgases formed in the acetic acid production process is directly or indirectly fed to the absorption column and subjected to the absorption step according to the present invention. Non-limiting examples of the offgas to be subjected to the absorption step according to the present invention include an offgas from a reactor in the after-mentioned reaction step; an offgas from an evaporator in the after-mentioned evaporation step; an offgas from a distillation column in the after-mentioned separation step; and an offgas from a distillation column in the after-mentioned acetaldehyde-removing system.

The absorption step according to the present invention is the step of bringing an offgas formed in the process into contact (in particular, countercurrent contact) with an absorbent to allow the absorbent to absorb an iodine compound from the offgas and whereby separating the offgas into a gas and a solution, where the gas has a lower iodine compound concentration as compared with the offgas, and the solution contains the absorbent and the iodine compound. Specifically, the offgas is continuously introduced into an absorption column with which the absorption step is performed; whereas the absorbent is continuously introduced into the absorption column through a line positioned at a higher height in the absorption column than the height at which the offgas is fed. In the column, the ascending offgas and the descending absorbent are brought into countercurrent contact with each other to allow the absorbent to absorb an iodine compound from the offgas. Thus, a gas having a lower iodine compound concentration as compared with the offgas, and a solution containing the iodine compound and the absorbent are to be separated.

The absorption step according to the present invention may be performed in one absorption column or two or more absorption columns. For example, assume that offgases from two or more processes are subjected to the absorption step. In this case, since the offgases are different typically in composition and/or pressure, the absorption step may be performed according to an adsorption process using two or more absorption columns (such as a high-pressure absorption column and a low-pressure absorption column). Also for example, assume that two or more iodine compounds are to be separated efficiently from the offgas. In this case, the absorption step may be performed so that two or more absorption columns using absorbents having different compositions are disposed in series, and the different absorption columns are allowed to absorb different iodine compounds.

Non-limiting examples of the iodine compound to be absorbed by the absorbent in the absorption step according to the present invention include iodine compounds present in the process, including hydrogen iodide; and alkyl iodides such as methyl iodide, ethyl iodide, and hexyl iodide. Among them, the iodine compound to be absorbed by the absorbent is preferably selected from hydrogen iodide, which may corrode the interior of distillation columns; and methyl iodide, which is a useful component usable in the reaction step. When hydrogen iodide is to be absorbed in the absorption step, the resulting gas has a very low hydrogen iodide concentration. This configuration impedes corrosion of the interior of an absorption column when another absorption step using the absorption column is further provided downstream from the above-mentioned absorption step. The configuration also impedes corrosion of the interior of a distillation column in the stripping step by which the solution is subjected to distillation. Thus, the absorption column and the distillation column can be made of a low-grade material or materials. Assume that methyl iodide is to be absorbed in the absorption step. In this case, methyl iodide can be separated and obtained by distillation of the solution in the stripping step, and can be recycled to the reactor and reused in the reaction step. Each of different iodine compounds may be absorbed alone or in combination in the absorption step.

The absorption step according to the present invention employs, as an absorbent, an organic acid having a higher boiling point as compared with acetic acid. The configuration of using, as the absorbent, such an organic acid having a higher boiling point as compared with acetic acid gives better separation efficiency in the step (stripping step) of separating methyl iodide by distillation, as compared with the case using acetic acid as the absorbent. This is because of a larger difference in boiling point between methyl iodide and the organic acid. For better separation efficiency, the configuration does not require operation of the distillation column at a high reflux ratio as with the case using acetic acid as the absorbent, and this can save the amount of steam for use in the reboiler at the distillation column and can also save energy. The absorbent may include each of different organic acids alone or in combination.

Non-limiting examples of the organic acid having a higher boiling point as compared with acetic acid include carboxylic acids having 3 or more carbon atoms; and hydrocarbon group-substituted sulfonic acids. Non-limiting examples of the carboxylic acids having 3 or more carbon atoms include propionic acid, butyric acid, and valeric acid. A non-limiting example of the hydrocarbon group-substituted sulfonic acids is methanesulfonic acid. The organic acid is preferably selected from carboxylic acids having 3 or more carbon atoms, and is more preferably propionic acid, from the viewpoints typically of good handleability and small effects on acetic acid. The absorbent may include each of different organic acids alone or in combination.

The organic acid is preferably selected from organic acids having a boiling point at atmospheric pressure of higher than acetic acid, and preferably 250° C. or lower (more preferably 220° C. or lower, furthermore preferably 200° C. or lower, furthermore preferably 190° C. or lower, furthermore preferably 180° C. or lower, furthermore preferably 170° C. or lower, furthermore preferably 160° C. or lower, and particularly preferably 150° C. or lower). The lower limit of the boiling point is typically 120° C., preferably 125° C., and more preferably 130° C., from the viewpoints of a large difference in boiling point from methyl iodide and good methyl iodide separation efficiency. In particular, the organic acid is preferably propionic acid.

The absorbent may further include one or more components other than the organic acid. Non-limiting examples of the other components include alcohols such as methanol; carboxylic esters such as methyl acetate; acetic acid, and other organic acids having boiling points lower than acetic acid, such as formic acid; ethers; ketones; water; basic aqueous solutions; hydrocarbons; as well as impurities present or formed in the acetic acid production process.

The organic acid in the absorbent is present in a concentration of typically 10 ppm by mass or more, preferably 20 ppm by mass or more, more preferably 50 ppm by mass or more, furthermore preferably 100 ppm by mass or more, and particularly preferably 200 ppm by mass or more, or may be present in a concentration of 300 ppm by mass or more, 400 ppm by mass or more, 500 ppm by mass or more, 1000 ppm by mass or more, 1 mass percent or more, 5 mass percent or more, 10 mass percent or more, 20 mass percent or more, 30 mass percent or more, 40 mass percent or more, 50 mass percent or more, 60 mass percent or more, 70 mass percent or more, 80 mass percent or more, or 90 mass percent or more. The upper limit of the concentration is 100 mass percent, but may be 99.999 mass percent, 99.99 mass percent, 99.9 mass percent, 99.5 mass percent, 99 mass percent, or 98 mass percent. The absorbent may have a propionic acid concentration falling within the range.

Hydrogen iodide includes molecular hydrogen iodide. When at least a portion of hydrogen iodide is ionized in a polar medium (generally a medium containing water), hydrogen iodide includes both molecular hydrogen iodide and dissociated hydroiodic acid. The two forms are convertible to each other. The hydrogen iodide concentration herein can be determined by potentiometric titration, or by subtraction technique in which the concentration is determined by subtracting other ionic iodides from the totality of ionic iodides.

By the potentiometric titration, the hydrogen iodide concentration is determined through acid-base titration using a potentiometric titration end-point. In particular, the hydrogen iodide concentration may be determined by performing titration to the potentiometric titration end-point typically with a standard lithium acetate solution. The subtraction technique is the technique of determining the hydrogen iodide concentration by subtracting the concentrations of iodides that are assumed to be involved in measurement of corrosion metals or non-hydrogen cations from the total concentration of all ionic iodides present in the sample.

The hydrogen iodide concentration in the solution, as determined by the subtraction technique, is typically 0.01 ppm by mass or more, or may be 0.1 ppm by mass or more, 1 ppm by mass or more, 10 ppm by mass or more, 50 ppm by mass or more, 100 ppm by mass or more, 200 ppm by mass or more, 300 ppm by mass or more, 400 ppm by mass or more, 500 ppm by mass or more, 600 ppm by mass or more, 700 ppm by mass or more, 800 ppm by mass or more, 900 ppm by mass or more, 1000 ppm by mass or more, 2000 ppm by mass or more, 3000 ppm by mass or more, 4000 ppm by mass or more, 5000 ppm by mass or more, 6000 ppm by mass or more, 7000 ppm by mass or more, 8000 ppm by mass or more, 9000 ppm by mass or more, or 1 mass percent or more. The hydrogen iodide concentration is typically 10 mass percent or less, or may be 5 mass percent or less, 3 mass percent or less, 2 mass percent or less, 1 mass percent or less, less than 1 mass percent, 5000 ppm by mass or less, or 3000 ppm by mass or less.

The hydrogen iodide concentration in the solution, as determined by the potentiometric titration, is typically 0.01 ppm by mass or more, or may be 0.1 ppm by mass or more, 1 ppm by mass or more, 10 ppm by mass or more, 50 ppm by mass or more, 100 ppm by mass or more, 200 ppm by mass or more, 300 ppm by mass or more, 400 ppm by mass or more, 500 ppm by mass or more, 600 ppm by mass or more, 700 ppm by mass or more, 800 ppm by mass or more, 900 ppm by mass or more, 1000 ppm by mass or more, 2000 ppm by mass or more, 3000 ppm by mass or more, 4000 ppm by mass or more, 5000 ppm by mass or more, 6000 ppm by mass or more, 7000 ppm by mass or more, 8000 ppm by mass or more, 9000 ppm by mass or more, or 1 mass percent or more. The hydrogen iodide concentration is typically 5 mass percent or less, and preferably 2 mass percent or less. The hydrogen iodide concentration is typically 10 mass percent or less, or may be 5 mass percent or less, 3 mass percent or less, 2 mass percent or less, 1 mass percent or less, less than 1 mass percent, 5000 ppm by mass or less, or 3000 ppm by mass or less.

The methyl iodide concentration in the solution is typically 1 ppm by mass or more, or may be 10 ppm by mass or more, 100 ppm by mass or more, 1000 ppm by mass or more, 5000 ppm by mass or more, or 1 mass percent or more. The methyl iodide concentration is typically 20 mass percent or less (e.g., 15 mass percent or less), and preferably 10 mass percent or less (e.g., 8 mass percent or less).

The acetic acid production method according to the present invention may further include another absorption step than the absorption step according to the present invention. The configurations of the other absorption step are the same as with those of the absorption step according to the present invention, except for using, as the absorbent, another component than the organic acid.

The acetic acid production method according to the present invention may include a stripping step (distillation step). The stripping step is the step of subjecting the solution from the absorption step to distillation. By the stripping step, the solution is subjected to distillation and is thereby separated into an overhead stream rich in components having lower boiling points as compared with the absorbent, and a bottom stream rich in the absorbent. The method, when including the stripping step, is excellent in economic efficiency, because the solution can be separated into useful components and the bottom stream rich in the absorbent, the useful components are recycled to the reactor, and the separated absorbent can be reused as an absorbent in the absorption step.

The methyl iodide concentration in a charge liquid to a distillation column in the stripping step is typically 1 ppm by mass or more, or may be 10 ppm by mass or more, 100 ppm by mass or more, 1000 ppm by mass or more, 5000 ppm by mass or more, or 1 mass percent or more. The methyl iodide concentration is typically 20 mass percent or less (e.g., 15 mass percent or less), and preferably 10 mass percent or less (e.g., 8 mass percent or less).

The hydrogen iodide concentration in the charge liquid to the distillation column in the stripping step, as determined by the subtraction technique, is typically 5 mass percent or less, or may be 4 mass percent or less, 3 mass percent or less, 2 mass percent or less, 1 mass percent or less, less than 1 mass percent, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, or 1 ppm by mass or less. The hydrogen iodide concentration is typically 0.0001 ppm by mass or more, or may be 0.001 ppm by mass or more, 0.01 ppm by mass or more, 0.1 ppm by mass or more, 0.5 ppm by mass or more, or 1 ppm by mass or more.

The hydrogen iodide concentration in the charge liquid to the distillation column in the stripping step, as determined by potentiometric titration, is typically 5 mass percent or less, or may be 4 mass percent or less, 3 mass percent or less, 2 mass percent or less, 1 mass percent or less, less than 1 mass percent, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, or 1 ppm by mass or less. The hydrogen iodide concentration is typically 0.0001 ppm by mass or more, or may be 0.001 ppm by mass or more, 0.01 ppm by mass or more, 0.1 ppm by mass or more, 0.5 ppm by mass or more, or 1 ppm by mass or more.

Non-limiting examples of the light ends to be concentrated in the overhead stream resulting from separation in the stripping step include iodine compounds (such as methyl iodide and hydrogen iodide), water, methyl acetate, dimethyl ether, methanol, acetaldehyde, and formic acid. At least a portion of the overhead stream, when including useful components such as methyl iodide, may be recycled to the reactor (reaction step). The recycling to the reactor allows the useful components to be reused in the reaction step, and this offers excellent economic efficiency. The overhead stream may also be recycled to one or more distillation steps (such as a light ends-removing step, a dehydration step, and a heavy ends-removing step) downstream from the evaporation step.

Assume that the offgas to be subjected to the absorption step is an offgas from a decanter for reserving a condensate resulting from condensation of an overhead stream from the light ends-removing step. In this case, the overhead stream from the stripping step may include a large amount of acetaldehyde. Accordingly, it is acceptable that the overhead stream from the stripping step is fed to the acetaldehyde-removing system or that the overhead stream is, before being recycled through the decanter to the reactor, fed to the acetaldehyde-removing system, and acetaldehyde is removed therefrom by the working of the acetaldehyde-removing system.

The methyl iodide concentration in the overhead stream from the stripping step is typically 5 mass percent or more, or may be 10 mass percent or more, 20 mass percent or more, 30 mass percent or more, 40 mass percent or more, 50 mass percent or more, 60 mass percent or more, 70 mass percent or more, or 80 mass percent or more. The upper limit of the methyl iodide concentration is typically 99.9 mass percent (e.g., 99 mass percent), preferably 98 mass percent (e.g., 95 mass percent), more preferably 93 mass percent (90 mass percent), or may be 80 mass percent, 70 mass percent, 60 mass percent, 50 mass percent, or 45 mass percent.

Of the bottom stream from the distillation column bottom, which is separated and obtained in the stripping step, at least a portion may be continuously discharged out of the system; and at least a portion may be cycled to the absorption column. At least a portion of the bottom stream may be recycled to at least one of the reaction step, the evaporation step, and a purification step downstream from the evaporation step.

Hereinafter, a scrubbing system according to one embodiment will be illustrated, where the scrubbing system includes the absorption step according to the present invention. FIG. 1 depicts an exemplary schematic flow chart illustrating a scrubbing system according to an embodiment of the present invention. The scrubbing system 8 includes an absorption column 81, an absorption column 82, and a distillation column 84. In the acetic acid production method according to the embodiment, an absorption step or steps are performed with the absorption columns 81 and 82; and a stripping step is performed with the distillation column 84. The absorption step according to the present invention is performed with at least one of, preferably both of, the absorption columns 81 and 82. The two absorption columns may employ an identical absorbent or different absorbents.

The absorption column 81 is a unit (high-pressure absorption column) to perform an absorption step of absorbing and recovering an iodine compound from, of offgases, a high-pressure gas. This absorption step is the step of bringing the high-pressure gas into contact with an absorbent to allow the absorbent to absorb an iodine compound from the high-pressure gas, and whereby a gas having a lower iodine compound concentration as compared with the high-pressure gas, and a solution containing the absorbent and the iodine compound are to be separated.

Specifically, the high-pressure gas is continuously introduced through a line 58 (high-pressure gas feed line) into the absorption column 81; whereas the absorbent is continuously introduced through a line 59 (absorbent feed line) into the absorption column 81, where the line 59 is positioned at a height higher than the high-pressure gas introducing height. In the column, the ascending high-pressure gas and the descending absorbent are brought into countercurrent contact with each other to allow the absorbent to absorb an iodine compound from the high-pressure gas. Thus, a gas having a lower iodine compound concentration as compared with the high-pressure gas, and a solution containing the iodine compound and the absorbent are to be separated. At the absorption column 81, the gas is obtained from the column top through a line 60; and the solution is obtained from the column bottom through a line 61.

A non-limiting example of the high-pressure gas is an offgas from the reactor (or the reaction step). The offgas discharged from the reactor may be fed directly through the line 58 to the absorption column 81; or may be fed as a non-condensable gas through the line 58 to the absorption column 81, where the non-condensable gas results from separation of the offgas, using a condenser, into a condensate and the non-condensable gas. The temperature of the absorbent before being fed to the absorption column 81 is typically 1° C. to 120° C. and is a temperature within such a range that the absorbent is neither frozen nor boiled.

The absorption column 81 is selected from rectification columns such as a plate column and a packed column. The packing in the packed column may be any of structured packings and dumped packings. The absorption column 81, when being a plate column, typically has 1 to 100 theoretical plates. The column internal pressure is typically from atmospheric pressure to 5 MPaG (gauge pressure) and is generally equal to or lower than the reactor internal pressure. The column internal temperature is typically about 1° C. to about 120° C.

The absorption column 82 is a unit (low-pressure absorption column) to preform an absorption step of absorbing and recovering an iodine compound from, of offgases, a low-pressure gas. This absorption step is the step of bringing the low-pressure gas into contact with an absorbent to allow the absorbent to absorb an iodine compound from the low-pressure gas, and whereby a gas having a lower iodine compound concentration as compared with the low-pressure gas, and a solution containing the absorbent and the iodine compound are to be separated.

Specifically, the low-pressure gas is continuously introduced through a line 62 (low-pressure gas feed line) into the absorption column 82; whereas the absorbent is continuously introduced through a line 63 (absorbent feed line) into the absorption column 82, where the line 63 is positioned at a height higher than the low-pressure gas feeding height. In the column, the ascending low-pressure gas and the descending absorbent are brought into countercurrent contact with each other to allow the absorbent to absorb an iodine compound from the low-pressure gas. Thus, a gas having a lower iodine compound concentration as compared with the low-pressure gas, and a solution containing the iodine compound and the absorbent are to be separated. At the absorption column 82, the gas is obtained from the column top through a line 64, and the solution is obtained from the column bottom through a line 65.

Non-limiting examples of the low-pressure gas include an offgas from the evaporator (or evaporation step); an offgas from the light ends column (or light ends-removing step); an offgas from a decanter for reserving a condensate resulting from condensation of the overhead stream rich in light ends from the light ends column; an offgas from the dehydration column (or dehydration step); and an offgas from the heavy ends column (or heavy ends-removing step). Each of these offgases may be fed through the line 62 to the absorption column 82 directly, or as a non-condensable gas resulting from separation, using a condenser, of the offgas into a condensate and the non-condensable gas. The temperature of the absorbent before being fed to the absorption column 82 is similar to the temperature of the absorbent before being fed to the absorption column 81.

The gas (line 60) from the column top of the absorption column 81, and the gas (line 64) from the column top of the absorption column 82 are gases from which useful components and hydrogen iodide have been collected and removed. These gases are merged with each other and discarded through a line 69. The gases discharged from the line 69 or from the lines 60 and 64 before merging are usable as a carbon monoxide (CO) source to be introduced into the bottom portion of the after-mentioned evaporator 2, or into residue stream recycle lines 18 and 19. On the other hand, the solution (line 61) from the column bottom of the absorption column 81 and the solution (line 65) from the column bottom of the absorption column 82 are merged with each other and fed through a line 68a to the distillation column 84.

The distillation column 84 is a unit to preform a stripping step. The stripping step (desorption step) in the embodiment is the step of separating, by distillation, the solution (line 68a) from the absorption column bottom into an overhead stream rich in useful components (in particular, methyl iodide), and a bottom stream rich in the absorbent. More specifically, the solution (line 68a) continuously introduced into the distillation column 84 is treated by distillation and separated into an overhead stream rich in useful components (in particular, methyl iodide), and bottoms rich in the absorbent. At the distillation column 84, vapors as the overhead stream are continuously drawn from the column top portion to a line 73; and the bottoms are continuously drawn from the column bottom portion to a line 74. There is disposed a reboiler 84b. The absorption step according to the present invention employs an organic acid having a higher boiling point as compared with acetic acid, and the solution to be subjected to distillation in the distillation column 84 includes the organic acid. Accordingly, separation in the distillation column 84 is relatively easy, and this reduces the amount of steam to be used in the reboiler 84b and saves energy, because the difference in boiling point between the organic acid and methyl iodide is relatively large.

The distillation column 84 is selected typically from rectification columns such as a plate column and a packed column. The overhead stream from the distillation column 84 is introduced through the line 73 into the condenser 84a. The condenser 84a cools and partially condenses the overhead stream from the distillation column 84 to separate the overhead stream into a condensate and a gas. Of the condensate, a portion is refluxed to the distillation column 84; and another portion is distilled out through a line 73b. In the embodiment illustrated in FIG. 1, a portion of the condensate is refluxed to the distillation column 84. However, the totality of the condensate may be distilled out through the line 73b. A non-condensable gas, which has not been condensed even by the working of the condenser 84a, may be fed through the line 73a, merged into the line 62, and cycled to the absorption column 82, or may be discarded, or may be recycled to a site immediately before a condenser for condensation of an overhead stream from the column top of a distillation column such as the light ends column, the dehydration column, or the heavy ends column. The recycled non-condensable gas may be cycled again through the line 62 to the absorption column 82 after a condensate is removed therefrom by the working of a condenser.

The overhead stream (line 73), which is rich in useful components (in particular, methyl iodide), from the column top of the distillation column 84 may be recycled to at least one of the reactor, the evaporator, and a distillation column disposed downstream from the evaporator. The recycling of the overhead stream to the reactor allows the useful components (in particular, methyl iodide) to be reused in the reaction step and gives excellent economic efficiency. When the offgas to be subjected to the absorption step is the offgas from the decanter, the overhead stream rich in useful components may include a large amount of acetaldehyde, because components having lower boiling points than the absorbent are concentrated in the overhead stream. Accordingly, it is acceptable that the overhead stream rich in useful components is fed to the acetaldehyde-removing system or that the overhead stream rich in useful components is, before being recycled through the decanter to the reactor, the overhead stream rich in useful components is fed to the acetaldehyde-removing system, and acetaldehyde is removed from the overhead stream by the working of the acetaldehyde-removing system. Of the bottom stream (line 74) from the column bottom of the distillation column 84, a portion is discharged continuously or batchwise through a line 75 out of the system; and the remainder is combined with a fresh absorbent fed continuously or batchwise through a line 76, and is cycled through a line 68b to the absorption columns 81 and 82, and is reused as the absorbent in the absorption step. It is also acceptable that the totality of the bottom stream (line 74) is discharged out of the system without cycling, and a fresh absorbent or absorbents are fed to the absorption columns 81 and 82. At least a portion (e.g., the solution discharged through the line 75 out of the system) of the bottom stream (line 74) may be recycled to at least one of the reactor, the evaporator, and a distillation column (such as the light ends column, the dehydration column, or the heavy ends column) downstream from the evaporator.

The distillation column 84, when being a plate column, typically has 1 to 50 theoretical plates, where the number of theoretical plates may be determined according to the composition of the solution to be subjected to distillation. The reflux ratio at the distillation column 84 is typically 3000 or less (e.g., 0 to 3000), or may be 1000 or less, 500 or less, 300 or less, 100 or less, 50 or less, 30 or less, 20 or less, 10 or less, 5 or less, or 3 or less, where the reflux ratio may be determined according to the number of theoretical plates. In the distillation column 84, the column top pressure is set typically to 1 to 500 kPaG; and the column bottom pressure is set to be higher than the column top pressure and to be typically 10 to 700 kPaG. In the distillation column 84, the column top temperature is set typically to a temperature which is lower than the boiling point of the absorbent at the set column top pressure and is typically 40° C. to 150° C.; and the column bottom temperature is set typically to a temperature which is equal to or higher than the boiling point of acetic acid at the set column bottom pressure and is 118° C. to 200° C. (preferably 120° C. to 190° C., more preferably 120° C. to 180° C., and furthermore preferably 120° C. to 170° C.)

FIG. 2 depicts an exemplary schematic flow chart illustrating a scrubbing system according to another embodiment, where the scrubbing system includes the absorption step according to the present invention. In this embodiment, the absorption step is performed only in the absorption column 81, and the gas from the column top of the absorption column 81 is discarded through the line 60, or is used as a carbon monoxide (CO) source to be introduced into the bottom portion of the evaporator 2 or into the residue stream recycle lines 18 and 19. In contrast, the solution (line 61) from the column bottom of the absorption column 81 is fed to the distillation column 84. The other configurations than these are as with the embodiment illustrated in FIG. 1.

The acetic acid production method according to the present invention may include a first absorption step and a second absorption step. By the first absorption step, at least a portion of offgases formed in the process is fed to an absorption column, the fed offgas is brought into contact with a first absorbent to allow the first absorbent to absorb an iodine compound from the offgas, and whereby a first gas having a lower iodine compound concentration as compared with the offgas, and a first solution containing the iodine compound and the first absorbent are to be separated. By the second absorption step, the first gas is, in an absorption column, brought into contact with a second absorbent being different in composition from the first absorbent, to allow the second absorbent to absorb an iodine compound from the first gas, and whereby a second gas having a lower iodine compound concentration as compared with the first gas, and a second solution containing the iodine compound and the second absorbent are to be separated. In this case, the absorption step according to the present invention is included in at least one of the first and second absorption steps.

When the method includes the first and second absorption steps, at least a portion of all offgases formed in the acetic acid production process is fed to an absorption column(s) and subjected to the first and second absorption steps. Non-limiting examples of the offgas to be subjected to the first and second absorption steps include an offgas from the reactor in the reaction step; an offgas from the evaporator in the evaporation step; an offgas from the distillation column in the separation step; and an offgas from the distillation column in the acetaldehyde-removing system.

Each of the first and second absorption steps may be performed in one absorption column, or in two or more absorption columns. For example, assume that offgases from two or more processes are subjected to the first absorption step. In this case, the first absorption step may be performed according to the adsorption technique using two or more absorption columns (such as a high-pressure absorption column and a low-pressure absorption column). This is because the offgases are different from each other typically in composition and/or in pressure. The first and second absorption steps may also be performed in a single absorption column.

The second absorbent is an absorbent differing in composition from the first absorbent. Non-limiting examples of the case just mentioned above include the case where a component not contained in one of the two absorbents is contained in the other absorbent; and the case where the two absorbents are identical in components, but different in content of at least one of the components. The two-stage absorption step using the two different absorbents having different compositions, i.e., the first and second absorbents, enables efficient separation and recovery of hydrogen iodide and methyl iodide each other. This is because the two different absorbents are different in solvent power to hydrogen iodide and to methyl iodide, thereby one absorption step using one of the absorbents gives a solution enriched with one of hydrogen iodide and methyl iodide, whereas the other absorption step using the other absorbent gives a solution enriched with the other of hydrogen iodide and methyl iodide as compared with the former solution.

The first absorption step is the step of bringing an offgas formed in the process into contact (in particular, countercurrent contact) with the first absorbent to allow the first absorbent to absorb an iodine compound from the offgas, and whereby a first gas having a lower iodine compound concentration as compared with the offgas, and a first solution containing the iodine compound and the first absorbent are to be separated. Specifically, the offgas is continuously introduced into an absorption column with which the first absorption step is performed; whereas the first absorbent is continuously introduced through a line into the absorption column, where the line is coupled to the absorption column at a height higher than the offgas feeding height. In the column, the ascending offgas and the descending first absorbent are brought into countercurrent contact with each other, to allow the first absorbent to absorb an iodine compound from the offgas. Thus, a first gas having a lower iodine compound concentration as compared with the offgas, and a first solution containing the iodine compound and the first absorbent are to be separated. The first absorption step may be performed using one absorption column or two or more absorption columns.

The second absorption step is the step of bringing the first gas, which has an iodine compound concentration lowered by the first absorption step, into contact (in particular, countercurrent contact) with the second absorbent and thereby a second gas having a lower iodine compound concentration as compared with the first gas, and a second solution containing the iodine compound and the second absorbent are to be separated. Specifically, the second absorbent is continuously introduced through a line into an absorption column with which the second absorption step is performed, where the line is coupled to the absorption column at a height higher than the first gas feeding height. In the column, the ascending first gas and the descending second absorbent are brought into countercurrent contact with each other, to allow the second absorbent to absorb an iodine compound from the first gas. Thus, a second gas having a lower iodine compound concentration as compared with the first gas, and a second solution containing the iodine compound and the second absorbent are to be separated. The second absorption step may be performed using one absorption column or two or more absorption columns. Assume that the first absorption step is performed using two or more absorption columns. In this case, first gases from the two or more absorption columns may be merged and then subjected to the second absorption step, or may be fed individually to one or more absorption columns and be subjected to the second absorption step. The first and second absorption steps may be performed using a single absorption column or using two or more different absorption columns.

Non-limiting examples of the iodine compounds to be absorbed by the absorbents in the first and second absorption steps are as with those exemplified above as the iodine compound to be absorbed in the absorption step according to the present invention. Among them, the iodine compounds are preferably hydrogen iodide and methyl iodide. In particular, it is preferred that the iodine compound to be absorbed in the first absorption step is hydrogen iodide, and the iodine compound to be absorbed in the second absorption step is methyl iodide. Assume that the first and second absorption steps are performed using different absorption columns. In this case, when hydrogen iodide is sufficiently absorbed in the first absorption step, the resulting first gas has a very low hydrogen iodide concentration. This less causes corrosion in an absorption column used in the second absorption step and allows the absorption column to be made of a material having low corrosion resistance (low-grade material). In addition, such significantly lowered hydrogen iodide concentration in the first gas to be fed to the second absorption step allows the resulting second solution to have a lower hydrogen iodide concentration, because hydrogen iodide is little absorbed by the second absorbent in the second absorption step. This less causes corrosion in the distillation column during distillation of the second solution in the stripping step, and allows the distillation column to be made of a low-grade material. Each of different iodine compounds may be absorbed alone or in combination in each of the first and second absorption steps.

Accordingly, it is preferred that at least one of the first absorbent and the second absorbent includes the organic acid having a higher boiling point as compare with acetic acid, and the other includes water or a basic aqueous solution. Specifically, it is preferred that at least one of the first absorption step and the second absorption step is the absorption step according to the present invention, and the other is an absorption step using an absorbent including water or a basic aqueous solution. Water, when used as or in one of the first absorbent and the second absorbent, can sufficiently absorb hydrogen iodide, because of having high solvent power to hydrogen iodide. The basic aqueous solution, when used as or in one of the first absorbent and the second absorbent, can sufficiently absorb hydrogen iodide, because water in the aqueous solution has high solvent power to hydrogen iodide, and, in addition, the basic aqueous solution can neutralize hydrogen iodide.

In particular, the first absorbent preferably includes water or a basic aqueous solution, from the viewpoint of high hydrogen iodide absorptivity; and the second absorbent preferably includes the organic acid having a higher boiling point as compared with acetic acid, from the viewpoint of high methyl iodide absorptivity. In this case, hydrogen iodide and methyl iodide can be efficiently separated from each other and individually recovered. This is because hydrogen iodide can be sufficiently recovered from the offgas by the action of the first absorbent in the first absorption step; whereas methyl iodide is little absorbed by the first absorbent, but can be sufficiently recovered by the action of the second absorbent in the second absorption step. The use of the first and second absorbents as above enables selective recovery/removal of hydrogen iodide and methyl iodide respectively in the first absorption step and in the second absorption step. This allows methyl iodide containing approximately no unnecessary hydrogen iodide and to be easily reused in the reactor. In addition, the configuration provides steam saving and energy saving during purification, by distillation, of the organic acid used as the absorbent in the second absorption step.

A preferred concentration of the organic acid having a higher boiling point as compared with acetic acid in the absorbent is as with the concentration of the organic acid in the absorbent for use in the absorption step according to the present invention.

The concentration of water in the water-containing absorbent is typically 10 ppm by mass or more, preferably 20 ppm by mass or more, more preferably 50 ppm by mass or more, furthermore preferably 100 ppm by mass or more, and particularly preferably 200 ppm by mass or more, or may be 300 ppm by mass or more, 400 ppm by mass or more, 500 ppm by mass or more, 1000 ppm by mass or more, 1 mass percent or more, 5 mass percent or more, 10 mass percent or more, 20 mass percent or more, 30 mass percent or more, 40 mass percent or more, 50 mass percent or more, 60 mass percent or more, 70 mass percent or more, 80 mass percent or more, or 90 mass percent or more. The upper limit of the concentration is 100 mass percent, but may be 99.999 mass percent, 99.99 mass percent, 99.9 mass percent, 99.5 mass percent, 99 mass percent, or 98 mass percent.

The hydrogen iodide concentration in the first solution, as determined by the subtraction technique, is typically 0.01 ppm by mass or more, or may be 0.1 ppm by mass or more, 1 ppm by mass or more, 10 ppm by mass or more, 50 ppm by mass or more, 100 ppm by mass or more, 200 ppm by mass or more, 300 ppm by mass or more, 400 ppm by mass or more, 500 ppm by mass or more, 600 ppm by mass or more, 700 ppm by mass or more, 800 ppm by mass or more, 900 ppm by mass or more, 1000 ppm by mass or more, 2000 ppm by mass or more, 3000 ppm by mass or more, 4000 ppm by mass or more, 5000 ppm by mass or more, 6000 ppm by mass or more, 7000 ppm by mass or more, 8000 ppm by mass or more, 9000 ppm by mass or more, or 1 mass percent or more. The hydrogen iodide concentration is typically 10 mass percent or less, or may be 5 mass percent or less, 3 mass percent or less, 2 mass percent or less, 1 mass percent or less, 5000 ppm by mass or less, or 3000 ppm by mass or less.

The hydrogen iodide concentration in the first solution, as determined by potentiometric titration, is typically 0.01 ppm by mass or more, or may be 0.1 ppm by mass or more, 1 ppm by mass or more, 10 ppm by mass or more, 50 ppm by mass or more, 100 ppm by mass or more, 200 ppm by mass or more, 300 ppm by mass or more, 400 ppm by mass or more, 500 ppm by mass or more, 600 ppm by mass or more, 700 ppm by mass or more, 800 ppm by mass or more, 900 ppm by mass or more, 1000 ppm by mass or more, 2000 ppm by mass or more, 3000 ppm by mass or more, 4000 ppm by mass or more, 5000 ppm by mass or more, 6000 ppm by mass or more, 7000 ppm by mass or more, 8000 ppm by mass or more, 9000 ppm by mass or more, or 1 mass percent or more. The hydrogen iodide concentration is typically 5 mass percent or less, and preferably 2 mass percent or less. The hydrogen iodide concentration is typically 10 mass percent or less, or may be 5 mass percent or less, 3 mass percent or less, 2 mass percent or less, 1 mass percent or less, 5000 ppm by mass or less, or 3000 ppm by mass or less.

The methyl iodide concentration in the first solution is typically 30 mass percent or less, or may be 25 mass percent or less, 20 mass percent or less, 15 mass percent or less, 10 mass percent or less, 7 mass percent or less, 5 mass percent or less, 4 mass percent or less, 3 mass percent or less, 2 mass percent or less, 1 mass percent or less, 5000 ppm by mass or less, 2000 ppm by mass or less, or 1000 ppm by mass or less. The methyl iodide concentration is typically 10 ppm by mass or more (e.g., 50 ppm by mass or more), preferably 100 ppm by mass or more (e.g., 500 ppm by mass or more), and more preferably 1000 ppm by mass or more (e.g., 2000 ppm by mass or more).

When the method includes two or more first absorption steps, the concentrations of the individual components in the first solution correspond to the concentrations of the individual components in all the first solutions separated and obtained in the two or more first absorption steps.

The hydrogen iodide concentration in the second solution, as determined by the subtraction technique, is preferably lower than the hydrogen iodide concentration in the first solution, is typically 5 mass percent or less, or may be 4 mass percent or less, 3 mass percent or less, 2 mass percent or less, 1 mass percent or less, less than 1 mass percent, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, 1 ppm by mass or less, or less than 1 ppm by mass. The hydrogen iodide concentration is typically 0.0001 ppm by mass or more, or may be 0.001 ppm by mass or more, 0.01 ppm by mass or more, 0.1 ppm by mass or more, or 0.5 ppm by mass or more.

The hydrogen iodide concentration in the second solution, as determined by potentiometric titration, is preferably lower than the hydrogen iodide concentration in the first solution, is typically 5 mass percent or less, or may be 4 mass percent or less, 3 mass percent or less, 2 mass percent or less, 1 mass percent or less, less than 1 mass percent, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, or 1 ppm by mass or less. The hydrogen iodide concentration is typically 0.0001 ppm by mass or more, or may be 0.001 ppm by mass or more, 0.01 ppm by mass or more, 0.1 ppm by mass or more, or 0.5 ppm by mass or more.

The methyl iodide concentration in the second solution is preferably higher than the methyl iodide concentration in the first solution, is typically 1 ppm by mass or more, or may be 10 ppm by mass or more, 100 ppm by mass or more, 1000 ppm by mass or more, 5000 ppm by mass or more, or 1 mass percent or more. The methyl iodide concentration is typically 20 mass percent or less (e.g., 15 mass percent or less), and preferably 10 mass percent or less (e.g., 8 mass percent or less).

When the method includes two or more second absorption steps, the concentrations of the individual components in the second solution correspond to the concentrations of the components in all the second solutions separated and obtained in the two or more second absorption steps.

The method, when including the first and second absorption steps, may include a distillation step (stripping step) of subjecting, to distillation, the first solution from the first absorption step and/or the second solution from the second absorption step. By the stripping step, the first and/or second solution is subjected to distillation and is separated into an overhead stream rich in components having lower boiling points than the first and/or second absorbent, and a bottom stream rich in the first and/or second absorbent. The method, when including the stripping step, is excellent in economic efficiency, because this configuration enables separation between useful components and the bottom stream rich in the first and/or second absorbent, allows the useful components to be recycled typically to at least one of the reactor, the evaporator, and the distillation columns, and allows the separated absorbent to be reused as an absorbent in the first and/or second absorption step.

Of the bottom stream, which is separated and obtained from the column bottom of the distillation column in the stripping step, at least a portion may be continuously discharged out of the system; and at least a portion may be cycled to at least one of the first and second absorption columns. At least a portion of the bottom stream may be recycled typically to at least one of the reactor, the evaporator, and a purification step (distillation step) provided downstream from the evaporator. Other preferred embodiments in the stripping step are as described above.

FIG. 3 depicts an exemplary schematic flow chart illustrating a scrubbing system according to an embodiment of the present invention, where the scrubbing system includes the first and second absorption steps. This scrubbing system 8 includes an absorption column 81, an absorption column 82, an absorption column 83, and a distillation column 84. The acetic acid production method according to the embodiment performs a first absorption step or steps in the absorption columns 81 and 82; a second absorption step in the absorption column 83; and a stripping step in the distillation column 84.

In the scrubbing system 8 illustrated in FIG. 3, the absorption step according to the present invention is performed in at least one of the absorption columns 81 to 83. At least one of the first absorption step(s) and the second absorption step is preferably the absorption step according to the present invention. When the first absorption step is the absorption step according to the present invention, the absorption steps in both the absorption columns 81 and 82 are each preferably the absorption step according to the present invention. The absorption columns 81 and 82 may employ an identical absorbent or different absorbents.

The absorption column 81 is a unit (high-pressure absorption column) to perform a first absorption step of absorbing and recovering an iodine compound from, of offgases, a high-pressure gas. This first absorption step is the step of bringing the high-pressure gas into contact with a first absorbent to allow the first absorbent to absorb an iodine compound from the high-pressure gas, and thereby a first gas having a lower iodine compound concentration as compared with the high-pressure gas, and a first solution containing the iodine compound and the first absorbent are to be separated.

Specifically, the high-pressure gas is continuously introduced through a line 58 (high-pressure gas feed line) to the absorption column 81; whereas the first absorbent is continuously introduced through a line 59 (first absorbent feed line) to the absorption column 81, where the line 59 is coupled to the absorption column 81 at a height higher than the high-pressure gas feeding height. In the column, the ascending high-pressure gas and the descending first absorbent are brought into countercurrent contact with each other, to allow the first absorbent to absorb an iodine compound from the high-pressure gas. Thus, the first gas having a lower iodine compound concentration as compared with the high-pressure gas, and the first solution containing the iodine compound and the first absorbent are to be separate. At the absorption column 81, the first gas is obtained from the column top through a line 60; and the first solution is obtained from the column bottom through a line 61.

A non-limiting example of the high-pressure gas is an offgas from the reactor (or reaction step). In this case, the offgas discharged from the reactor may be fed through the line 58 to the absorption column 81 directly, or as a non-condensable gas resulting from separation, using a condenser, of the offgas into a condensate and the non-condensable gas. The temperature of the first absorbent before being fed to the absorption column 81 is typically 1° C. to 120° C. and is a temperature within such a range that the first absorbent is neither frozen nor boiled.

The absorption column 81 is selected from rectification columns such as a plate column and a packed column. The packing in the packed column may be any of structured packings and dumped packings. The absorption column 81, when being a plate column, typically has 1 to 100 theoretical plates. The column internal pressure is typically from atmospheric pressure to 5 MPaG and is generally equal to or lower than the reactor internal pressure. The column internal temperature is typically about 1° C. to about 120° C.

The absorption column 82 is a unit (low-pressure absorption column) to perform a first absorption step of absorbing and recovering an iodine compound from, of offgases, a low-pressure gas. This first absorption step is the step of bringing the low-pressure gas into contact with the first absorbent to allow the first absorbent to absorb an iodine compound from the low-pressure gas, and thereby a first gas having a lower iodine compound concentration as compared with the low-pressure gas, and a first solution containing the iodine compound and the first absorbent are to be separated.

Specifically, the low-pressure gas is continuously introduced through a line 62 (low-pressure gas feed line) into the absorption column 82; whereas the first absorbent is continuously introduced through a line 63 (first absorbent feed line) into the absorption column 82, where the line 63 is coupled to the absorption column 82 at a height higher than the low-pressure gas feeding height. In the column, the ascending low-pressure gas and the descending first absorbent are brought into countercurrent contact with each other, to allow the first absorbent to absorb an iodine compound from the low-pressure gas. Thus, the first gas having a lower iodine compound concentration as compared with the low-pressure gas, and the first solution containing the iodine compound and the first absorbent are to be separated. At the absorption column 82, the first gas is obtained from the column top through a line 64, and the first solution is obtained from the column bottom through a line 65.

Non-limiting examples of the low-pressure gas include an offgas from the evaporator (or evaporation step); an offgas from the light ends column (or light ends-removing step); an offgas from a decanter for reserving a condensate resulting from condensation of the overhead stream rich in light ends from the light ends column; an offgas from the dehydration column (or dehydration step); and an offgas from the heavy ends column (or heavy ends-removing step). Each of these offgases may be fed through the line 62 to the absorption column 82 directly, or as a non-condensable gas resulting from separation, using a condenser, of the offgas into a condensate and the non-condensable gas. The temperature of the first absorbent before being fed to the absorption column 82 is as with the temperature of the first absorbent before being fed to the absorption column 81.

The absorption column 82 is selected from rectification columns such as a plate column and a packed column. The packing in the packed column may be any of structured packings and dumped packings. The absorption column 82, when being a plate column, typically has 1 to 100 theoretical plates. The column internal pressure is typically from atmospheric pressure to 5 MPaG and is generally equal to or lower than the reactor internal pressure. The column internal temperature is typically about 1° C. to about 120° C.

The first gas (line 60) from the column top of the absorption column 81 and the first gas (line 64) from the column top of the absorption column 82 are merged with each other and fed through the line 69 to the absorption column 83 with which the second absorption step is performed. On the other hand, the first solution (line 61) from the column bottom of the absorption column 81 and the first solution (line 65) from the column bottom of the absorption column 82 are merged with each other, a portion of which is discharged through a line 66 out of the system continuously or batchwise; whereas the remainder is combined with a fresh first absorbent fed through a line 67 continuously or batchwise. The resulting mixture is fed through a line 68, divided into the lines 59 and 63, and cycled respectively to the absorption columns 81 and 82, and reused as the first absorbent in the first absorption step(s). It is also acceptable that all the first solutions are discharged out of the system without cycling, and a fresh first absorbent is fed to the absorption columns 81 and 82. At least a portion (e.g., the first solution discharged out of the system through the line 66) of the first solutions may be recycled to at least one of the reactor, the evaporator, and a distillation column with which a distillation step is performed. For example, assume that the first absorbent includes water. In this case, the first absorbent efficiently absorbs hydrogen iodide, and almost all the first solution is cycled to the first absorption columns and reused as the first absorbent, and when hydrogen iodide is concentrated, a portion of the first solution is recycled to the reactor. This is because water in the reactor is consumed by the shift reaction with carbon monoxide ($H_2O+CO\rightarrow H_2+CO_2$). Water, when contained in a large amount in the first solution, may not be sufficiently consumed in the reactor, and the first solutions may be recycled to at least one of the aqueous phase in the decanter, the dehydration column, and the heavy ends column, instead of, or in addition to, being recycled to the reactor. In this case, the component in the first solution is concentrated typically in the aqueous phase in the decanter, at the column top of the dehydration column, and at the column top of the heavy ends column; and, of the resulting substance, a portion is recycled to the reactor, and another portion is discharged out of the system. The embodiment illustrated in FIG. 3 employs the same first absorbent in both the absorption columns 81 and 82. However, in another embodiment, the method may employ different first absorbents and subject the different first absorbents typically to cycling, discharging out of the system, and/or recycling.

The absorption column 83 is a unit (generally, a low-pressure absorption column) to perform a second absorption step of absorbing and recovering an iodine compound from the first gas from the first absorption step. This second absorption step is the step of bringing the first gas into contact with the second absorbent to allow the second absorbent to absorb an iodine compound from the first gas, and thereby a second gas having a lower iodine compound concentration as compared with the first gas, and a second solution containing the iodine compound and the second absorbent are to be separated.

Specifically, the first gas is continuously introduced through the line 69 into the absorption column 83, whereas the second absorbent is continuously introduced through a line 70 (second absorbent feed line) into the absorption column 83, where the line 70 is coupled to the absorption column 83 at a height higher than the first gas feeding height. In the column, the ascending first gas and the descending second absorbent are brought into countercurrent contact with each other, to allow the second absorbent to absorb an iodine compound from the first gas. Thus, the second gas having a lower iodine compound concentration as compared with the first gas, and the second solution containing the iodine compound and the second absorbent are to be separated. At the absorption column 83, the second gas is obtained from the column top through a line 71, and the second solution is obtained from the column bottom through a line 72. The temperature of the second absorbent before being fed to the absorption column 83 is typically 1° C. to 120° C. and is a temperature within such a range that the second absorbent is neither frozen nor boiled.

The second gas (line 71) from the column top of the absorption column 83 is discarded, because the second gas is a gas from which useful components have been collected and removed. The gas discharged from the line 71 is usable as a carbon monoxide source to be introduced into the bottom portion of the evaporator 2, or into the residue stream recycle lines 18 and 19. The second solution (line 72) from the column bottom of the absorption column 83 is fed to the distillation column 84.

The absorption column 83 is selected from rectification columns such as a plate column and a packed column. The packing in the packed column may be any of structured packings and dumped packings. The absorption column 83, when being a plate column, typically has 1 to 100 theoretical plates. The column internal pressure is typically from atmospheric pressure to 5 MPaG and is generally equal to or lower than the reactor internal pressure. The column internal temperature is typically about 1° C. to about 120° C.

The distillation column 84 is a unit with which a stripping step is performed. The stripping step in the embodiment is the step of separating, by distillation, the second solution into an overhead stream rich in useful components (in particular, methyl iodide), and a bottom stream rich in the second absorbent. At the distillation column 84, vapors as the overhead stream are continuously drawn from the column top portion to a line 73; and bottoms are continuously drawn from the column bottom portion to a line 74. There is disposed a reboiler 84*b*.

More specifically, the second solution continuously introduced into the distillation column 84 is subjected to distillation treatment and separated into the overhead stream rich in useful components (in particular, methyl iodide), and the bottoms rich in the second absorbent. The distillation column 84 is selected typically from rectification columns such as a plate column and a packed column. The overhead stream from the distillation column 84 is introduced through the line 73 into a condenser 84*a*. The condenser 84*a* cools and partially condenses the overhead stream from the distillation column 84 into a condensate and a gas. Of the condensate, a portion is refluxed to the distillation column 84, and another portion (or the remainder) is distilled through a line 73*b*. In the embodiment illustrated in FIG. 3, the condensate is refluxed to the distillation column 84, but the whole quantity of the condensate may be distilled out through the line 73*b*. The non-condensable gas, which has not been condensed by the working of the condenser 84*a*, may be fed through the line 73*a*, merged into the line 62, and cycled to the absorption column 82, or may be discarded, or may be recycled to a site immediately upstream from a condenser for condensation of an overhead stream from the column top of a distillation column such as the light ends column, the dehydration column, or the heavy ends column. It is also acceptable that the recycled non-condensable gas is then subjected to separation from a condensate by condensation using a condenser, and cycled again through the line 62 to the absorption column 82.

The overhead stream (line 73), which is rich in useful components (in particular, methyl iodide), from the column top of the distillation column 84 may be recycled typically to at least one of the reactor, the evaporator, and distillation columns disposed downstream from the evaporator. The recycling of the overhead stream to the reactor allows the useful components (in particular, methyl iodide) to be reused in the reaction step and gives excellent economic efficiency. Assume that the offgas to be subjected to the first absorption step is the offgas from the decanter. In this case, the overhead stream rich in useful components may include a large amount of acetaldehyde, because components having lower boiling points as compared with the second absorbent are concentrated in the overhead stream. Accordingly, it is acceptable that, before being recycled through the decanter to the reactor, the overhead stream rich in useful components is fed to the acetaldehyde-removing system, and acetaldehyde is removed therefrom by the working of the acetaldehyde-removing system. Of the bottom stream (line 74) from the column bottom of the distillation column 84, a portion is discharged though a line 75 out of the system continuously or batchwise; and the remainder is combined with a fresh second absorbent fed through a line 76 continuously or batchwise, is cycled through the line 70 to the absorption column 83, and is reused as the second absorbent in the second absorption step. It is also acceptable that the whole quantity of the second solution is discharged out of the system, and a fresh second absorbent is fed to the absorption column 83. At least a portion (e.g., the second solution discharged through the line 75 out of the system) of the second solution may be recycled typically to at least one of the reactor, the evaporator, the light ends column, the dehydration column, and the heavy ends column.

Preferred conditions for the distillation column 84, when being a plate column, are as with the conditions for the distillation column 84 illustrated in FIG. 1.

FIG. 4 depicts an exemplary schematic flow chart illustrating a scrubbing system according to another embodiment, where the scrubbing system includes the first and second absorption steps. In this embodiment, the first absorption step is performed only with the absorption column 81. At the absorption column 81, the first gas from the column top is fed through the line 60 to the absorption column 83 with which the second absorption step is performed; and the first solution is drawn from the column bottom through the line 61. A portion of the first solution is discharged (line 66) out of the system; and the remainder is combined with a fresh first absorbent (line 67), and is recycled, as the first absorbent, through the line 59 again to the absorption column 81. The other configurations than these are as with the embodiment illustrated in FIG. 3.

FIG. 5 depicts an exemplary schematic flow chart illustrating a scrubbing system according to yet another embodiment, where the scrubbing system includes the first and second absorption steps. In this embodiment, the first and second absorption steps are performed with a single absorption column 85. Specifically, in the first absorption step, an offgas from the process is continuously introduced through a line 77 (offgas feed line) into the absorption column 85; whereas the first absorbent is continuously introduced through a line 78 (first absorbent feed line) into the absorption column 85, where the line 78 is coupled to the absorption column 85 at a height higher than the offgas feeding height. In the column, the ascending offgas and the descending first absorbent are brought into countercurrent contact with each other, to allow the first absorbent to absorb an iodine compound from the offgas. Thus, a first gas having a lower iodine compound concentration as compared with the offgas, and a first solution containing the iodine compound and the first absorbent are to be separated. At the absorption column 85, the first gas further ascends in the column, whereas the first solution is discharged from the column bottom through a line 79. In the second absorption step, at the absorption column 85, the first gas further goes up in the column higher than the first absorbent feeding height, whereas the second absorbent is continuously introduced through a line 86 coupled to a portion adjacent to the column top of the absorption column 85. In the column, the ascending first gas and the descending second absorbent are brought into countercurrent contact with each other, to allow the second absorbent to absorb an iodine compound from the first gas. Thus, a second gas having a lower iodine compound concentration as compared with the first gas, and a second solution containing the iodine compound and the second absorbent are to be separated. At the absorption column 85, the second gas is drawn from the column top through a line 89, and the second solution is collected on a unit 87 and drawn through a line 88, where the unit 87 is capable of receiving a liquid falling down from the second absorbent feeding height and is exemplified typically by a chimney tray. From the absorption column 85, the second solution is fed through a line 88 to a distillation column 84 with which a stripping step is performed; and the first solution is drawn from the column bottom through the line 79. Of the first solution, a portion (line 90) is discharged out of the system; and the remainder is combined with e fresh first absorbent (line 90') and recycled as the first absorbent through a line 78 to the absorption column 85. Of the bottom stream (line 74) from the column bottom of the distillation column 84, a portion is discharged through the line 75 out of the system continuously or batchwise; and the remainder is combined with a fresh second absorbent fed through the line 76 continuously or batchwise, is cycled through the line 86 to the absorption column 85, and is reused as the second absorbent in the second absorption step. The other configurations than these are as with the embodiment illustrated in FIG. 3. Specifically, the second solution from the absorption column 85 is fed to the stripping step, but at least one of the first and second solutions may be recycled to at least one site in the process.

The acetic acid production method according to the present invention may include, in the acetic acid production process, a carbonylation step (reaction step) and a separation step. In the carbonylation step, methanol is reacted with carbon monoxide to form acetic acid. In the separation step, a reaction mixture from the carbonylation step is separated, using at least one selected from evaporators and distillation columns, into a stream including the metal catalyst, an acetic acid stream rich in acetic acid, and a stream richer in light ends than the acetic acid stream. The separation step preferably includes, for example, an evaporation step and a light ends-removing step. In the evaporation step, the reaction mixture from the carbonylation step is separated, using an evaporator, into a vapor stream and a residue stream. In the light ends-removing step, the vapor stream is separated, by distillation, into an overhead stream rich in light ends, and a first acetic acid stream rich in acetic acid. The separation step may include a dehydration step. In the dehydration step, the first acetic acid stream is separated, by distillation, into an overhead stream rich in water, and a second acetic acid stream richer in acetic acid than the first acetic acid stream.

Instead of the evaporation step and the light ends-removing step, the separation step may include an evaporation-light ends-removing step. This step is the step of separating the reaction mixture from the carbonylation step into a stream including the catalyst, an overhead stream rich in light ends, and a first acetic acid stream rich in acetic acid. Instead of the light ends-removing step and the dehydration step, the separation step may include a so-called light ends-removing-dehydration step which is a light ends-removing step that also functions as dehydration step. Namely, this step is the step of separating, by distillation, the vapor stream into an overhead stream rich in light ends, and an acetic acid stream which has been dehydrated to a water concentration at a similar level to that in the second acetic acid stream. Accordingly, the evaporation-light ends-removing step may be one that functions also as the dehydration step (an evaporation-light ends-removing-dehydration step). Acetic acid streams rich in acetic acid from the light ends-removing-dehydration step and the evaporation-light ends-removing-dehydration step correspond to the second acetic acid stream.

The acetic acid production method according to the present invention may further include at least one step selected from steps (a), (b), and (c) as follows.

The step (a) is a heavy ends-removing step of separating, by distillation, the first or second acetic acid stream into a bottom stream rich in heavy ends, and a third acetic acid stream richer in acetic acid than the acetic acid stream before being subjected to the distillation.

The step (b) is an adsorptive removing step of treating the first or second or third acetic acid stream with an ion exchange resin to give a fourth acetic acid stream.

The step (c) is a product step of subjecting the first or second or third or fourth acetic acid stream to distillation to give a fifth acetic acid stream richer in acetic acid than the acetic acid stream before being subjected to the distillation.

The acetic acid production method according to the present invention may include an acetaldehyde-removing system (acetaldehyde-removing step). In the acetaldehyde-removing system, acetaldehyde is separated, using a distillation column or columns, from at least a portion of a condensate resulting from condensation of the overhead stream rich in light ends.

In the acetic acid production method according to the present invention as above, at least one offgas is preferably fed to an absorption column, to be subjected to the absorption step according to the present invention or the first absorption step, where the at least one offgas is selected from the group consisting of an offgas from the reactor, an offgas from the evaporator, an offgas from the distillation column(s) in the separation step, and an offgas from the distillation column(s) in the acetaldehyde-removing system.

In the acetic acid production method according to the present invention as above, the overhead stream rich in methyl iodide separated and obtained in the stripping step may be recycled to at least one of the reaction step, the evaporation step, and distillation steps, for allowing methyl iodide to be advantageously reused in the reaction step in the reactor.

The acetic acid production method according to the present invention employs the absorbent including an organic acid having a higher boiling point as compared with acetic acid and gives a bottom stream rich in the organic acid as a result of separation in the stripping step. This bottom stream rich in the organic acid may be recycled to at least one of the reaction step, the evaporation step, and the distillation step. In particular, the bottom stream rich in the organic acid is preferably recycled to the charge to the dehydration column and/or to the charge to the heavy ends column. This is because heavy ends and light ends other than the organic acid can be removed by distillation in the dehydration column(s), and the organic acid can be concentrated and removed through the column bottom of the heavy ends column. The bottom stream rich in the organic acid, when including not so large amounts of impurities (such as the iodine compounds) other than the absorbent(s) and acetic acid, may be mixed with the acetic acid product, or may be recycled to at least one of the reactor, the evaporator, and the light ends column.

Assume that the acetic acid production method according to the present invention employs a water-containing absorbent. In this case, the resulting water-containing solution (aqueous solution) from the absorption step is preferably recycled to at least one apparatus selected from the group consisting of the reactor, a decanter for reserving the condensate, the dehydration column, and the heavy ends column. This is because water in the reactor is consumed by the shift reaction with carbon monoxide ($H_2O+CO \rightarrow H_2+CO_2$). The water-containing solution, when recycled to the aqueous phase in the decanter, is to be treated together with the aqueous phase. The water in the solution, when recycled to the dehydration column, is concentrated at the column top of the dehydration column; and when recycled to the heavy ends column, is concentrated at the column top of the heavy ends column. Such concentrated water is then recycled, or discarded.

Hereinafter, one embodiment of the acetic acid production method according to the present invention will be illustrated. FIG. 6 depicts an exemplary production flow chart (methanol carbonylation process) of an acetic acid production system according to an embodiment. Acetic acid production equipment according to the acetic acid production flow includes a reactor 1, an evaporator 2, a distillation column 3, a decanter 4, a distillation column 5, a distillation column 6, an ion exchange resin column 7, a scrubbing system 8, an acetaldehyde-removing system 9, condensers 1a, 2a, 3a, 5a, and 6a, a heat exchanger 2b, reboilers 3b, 5b, and 6b, lines 11 to 56, and a pump 57. The equipment is configured so as to be capable of producing acetic acid continuously.

In the acetic acid production method according to the embodiment, a reaction step, an evaporation step (flash step), a first distillation step, a second distillation step, a third distillation step, and an adsorptive removing step are performed respectively in the reactor 1, the evaporator 2, the distillation column 3, the distillation column 5, the distillation column 6, and the ion exchange resin column 7. The first distillation step, the second distillation step, and the third distillation step are also referred to respectively as a light ends-removing step, a dehydration step, and a heavy ends-removing step. Steps in the embodiment are not limited to those mentioned above. In particular, the equipment may not include one or more facilities such as the distillation column 5, the distillation column (heavy ends column) 6, the ion exchange resin column 7, and the acetaldehyde-removing system 9 (such as an acetaldehyde-removing column). The equipment may further include a product column disposed downstream from the ion exchange resin column 7, as described later.

The reactor 1 is a unit with which the reaction step is performed. The reaction step (carbonylation step) is the step of continuously forming acetic acid through a reaction (methanol-carbonylation reaction) represented by Chemical Formula (1) below. During steady operation of the acetic acid production equipment, the reactor 1 contains or houses a reaction mixture, which is stirred typically with a stirrer. The reaction mixture includes starting materials methanol and carbon monoxide, a metal catalyst, a promoter, water, production target acetic acid, and various by-products. In the reaction mixture, a liquid phase and a gas phase are in an equilibrium state. Chemical Formula (1) is expressed as follows:

$$CH_3OH + CO \rightarrow CH_3COOH \tag{1}$$

The starting materials in the reaction mixture are liquid methanol and gaseous carbon monoxide. Methanol is fed from a methanol storage unit (not shown) through the line 11 to the reactor 1 continuously at a predetermined flow rate. Carbon monoxide is fed from a carbon monoxide storage unit (not shown) through the line 12 to the reactor 1 continuously at a predetermined flow rate. The carbon monoxide does not always have to be pure carbon monoxide and may include a small amount (typically 5 mass percent or less, and preferably 1 mass percent or less) of one or more other gases such as nitrogen, hydrogen, carbon dioxide, and oxygen gases.

The metal catalyst in the reaction mixture is used to promote or accelerate the methanol-carbonylation reaction and may be selected typically from rhodium catalysts and iridium catalysts. A non-limiting example of the rhodium catalysts is a rhodium complex represented by the chemical formula: $[Rh(CO)_2I_2]^-$. A non-limiting example of the iridium catalysts is an iridium complex represented by the chemical formula: $[Ir(CO)_2I_2]^-$. The metal catalyst is preferably selected from metal complex catalysts. The catalyst may be present in the reaction mixture in a concentration (in terms of metal) of typically 200 to 10000 ppm by mass, preferably 300 to 5000 ppm by mass, and furthermore preferably 400 to 2500 ppm by mass, relative to the totality of the liquid phase of the reaction mixture (liquid reaction mixture).

The promoter is an iodide to assist the action of the catalyst and may be selected typically from methyl iodide and ionic iodides. Methyl iodide can offer the action of promoting the catalysis of the catalyst. Methyl iodide may be present in a concentration of typically 1 to 20 mass percent, and preferably 5 to 15 mass percent, relative to the totality of the liquid phase of the reaction mixture. The ionic iodides are iodides that form iodide ions in the liquid reaction mixture, of which ionic metal iodides are typified. The ionic iodides can offer the action of stabilizing the catalyst and/or the action of restraining side reactions. Non-limiting examples of the ionic iodides include alkali metal iodides such as lithium iodide, sodium iodide, and potassium iodide. The ionic iodide(s) may be present in the reaction mixture in a concentration of typically 1 to 25 mass percent, and preferably 5 to 20 mass percent, relative to the totality of the liquid phase of the reaction mixture. For example, when an iridium catalyst is used, a ruthenium compound and/or an osmium compound may be used as the promoter. These compounds may be used in a total amount of typically 0.1 to 30 moles (in terms of metal), and preferably 0.5 to 15 moles (in terms of metal), per mole (in terms of metal) of iridium.

Water in the reaction mixture is a component necessary for the formation of acetic acid, due to the reaction mechanism of the methanol-carbonylation reaction, and is a component necessary for dissolving water-soluble components in the reaction system. Water may be present in the reaction mixture in a concentration of typically 0.1 to 15 mass percent, preferably 0.5 to 10 mass percent, more preferably 1 to 6 mass percent, and furthermore preferably 1.5 to 4 mass percent, relative to the totality of the liquid phase of the reaction mixture. The water concentration is preferably 15 mass percent or less, so as to minimize energy necessary for removing water in the acetic acid purification process and for performing the acetic acid production more efficiently. To control the water concentration, water may be fed to the reactor 1 continuously at a predetermined flow rate.

Acetic acid in the reaction mixture includes acetic acid that has been charged into the reactor 1 before operation of the acetic acid production equipment; and acetic acid that is formed as a main product of the methanol-carbonylation reaction. Acetic acid as above can function as a solvent in the reaction system. Acetic acid may be present in the reaction mixture in a concentration of typically 50 to 90 mass percent, and preferably 60 to 80 mass percent, relative to the totality of the liquid phase of the reaction mixture.

A non-limiting example of major by-products contained in the reaction mixture is methyl acetate. Methyl acetate can be formed through reaction between acetic acid and methanol. Methyl acetate may be present in the reaction mixture in a concentration of typically 0.1 to 30 mass percent, and preferably 1 to 10 mass percent, relative to the totality of the liquid phase of the reaction mixture.

Another non-limiting example of the by-products contained in the reaction mixture is hydrogen iodide. When the catalyst with or without the promoter as above is used, hydrogen iodide is unavoidably formed due to the reaction mechanism of the methanol-carbonylation reaction. Hydrogen iodide may be present in the reaction mixture in a concentration of typically 0.01 to 2 mass percent, relative to the totality of the liquid phase of the reaction mixture.

Non-limiting examples of the by-products also include hydrogen, methane, carbon dioxide, acetaldehyde, crotonaldehyde, 2-ethylcrotonaldehyde, dimethyl ether, alkanes, formic acid, and propionic acid, as well as alkyl iodides such as hexyl iodide and decyl iodide. The reaction mixture may also include metals resulting from corrosion of the equipment, such as iron, nickel, chromium, manganese, and molybdenum (such metals are hereinafter also referred to as "corrosion metals"); and other metals such as cobalt, zinc, and copper. The corrosion metals and other metals are collectively also referred to as "metals such as corrosion metals".

In the reactor 1 housing the reaction mixture as above, the reaction temperature is set typically to 150° C. to 250° C., the reaction pressure as a total pressure is set typically to 1.5 to 3.5 MPa (absolute pressure), and the carbon monoxide partial pressure is set typically to 0.4 to 1.8 MPa (absolute pressure), preferably 0.6 to 1.6 MPa (absolute pressure), and furthermore preferably 0.9 to 1.4 MPa (absolute pressure).

Vapors in the gas phase in the reactor 1 during operation of the equipment typically include carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. The vapors can be drawn from the reactor 1 through the line 13. The inside pressure of the reactor 1 can be controlled by regulating the amount of the vapors to be drawn out, and is typically held constant. The vapors drawn from the reactor 1 are introduced into the condenser 1a.

The condenser 1a cools and partially condenses the vapors from the reactor 1 to separate the vapors into a condensate and a gas. The condensate typically includes methyl iodide, hydrogen iodide, water, methyl acetate, acetic acid, dimethyl ether, methanol, acetaldehyde, formic acid, and propionic acid. The condensate is introduced and recycled from the condenser 1a through the line 14 to the reactor 1. The gas typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 1a through the line 15 to the scrubbing system 8.

In the embodiment illustrated in FIG. 6, all of a gas (line 20) from the condenser 2a, a gas (line 32) from the condenser 3a, a gas (line 37) from the condenser 5a, and a gas (line 45) from the condenser 6a are merged into the line 15 and fed to the scrubbing system 8 (pattern A). However, it is also acceptable that only the gas from the condenser 1a is fed through the line 15 to the scrubbing system 8; and all the gases (lines 32, 37, and 45) from the condensers 3a, 5a, and 6a are merged into the line 20 and fed to the scrubbing system 8 (pattern B). In the pattern A, for example, the gas from the condenser 1a is fed through the line 15, and through the line 58 in the scrubbing system 8 illustrated in FIG. 2 or FIG. 4, or through the line 77 in the scrubbing system 8 illustrated in FIG. 5, to the absorption column 81 or the absorption column 85. In the pattern B, for example, the gas from the condenser 1a is fed through the line 15 and through the line 58 in the scrubbing system 8 illustrated in FIG. 1 or FIG. 3 to the absorption column 81; whereas the gas fed through the line 20 is fed through the line 62 in the scrubbing system 8 illustrated in FIG. 1 or FIG. 3, to the absorption column 82.

By the working of the scrubbing system 8, useful components (such as methyl iodide, methanol, dimethyl ether, water, methyl acetate, and acetic acid) are separated and recovered from the gas from the condenser 1a (line 15), through the absorption step according to the present invention, and, as needed, further through the stripping step, as described above. In the embodiment, the separation and recovery employs a wet process which is performed using an absorbing liquid (absorbent) for collecting useful components from a gas. For example, a condensate derived from vapors from the after-mentioned distillation column 6 is usable as the absorbing liquid. The separated and recovered useful components (such as methyl iodide) are introduced and recycled from the scrubbing system 8 (in particular, through the line 73 from the column top of the distillation column 84 in the stripping step) through the recycle line 48 to the reactor 1. Though not shown in the figure, it is also acceptable that the line 48 is introduced (coupled) to charge lines of the condensers 1a, 2a, 3a, and 5a, and whereby the useful components are cooled, condensed, and recovered. Gases (e.g., the line 69 in FIG. 1, and the line 60 in FIG. 2) from which useful components have been collected are discarded without further treatment, or used as a carbon monoxide source to be introduced into the bottom portion of the evaporator 2 or into the residue stream recycle lines 18 and 19. Gases (e.g., the line 71 in FIG. 3 and FIG. 4) from which useful components have been collected are discarded through the line 49. Gases (e.g., the lines 73a and 89 in FIG. 5) from which useful components have been collected may be subjected to separation of condensable components (condensates) therefrom using a condenser, and/or be recycled to the absorption column. The gas discharged from the line 49 is usable as a carbon monoxide source to be introduced into the bottom portion of the evaporator 2 or into the residue stream recycle lines 18 and 19. The treatment in the scrubbing system 8, and the subsequent recycling and discarding are applicable La the after-mentioned gases (lines 20, 32, 37, and 45) to be fed to the scrubbing system 8 from other condensers.

In the reactor 1 during operation of the equipment, acetic acid is continuously formed as described above. A reaction mixture containing such acetic acid is continuously drawn from the reactor 1 at a predetermined flow rate, and introduced through the line 16 into the subsequent (downstream) evaporator 2.

The evaporator 2 is a unit with which the evaporation step (flash step) is performed. The evaporation step is the step of partially evaporating the reaction mixture to separate the reaction mixture into a vapor stream (volatile phase) and a residue stream (low volatile phase; residual liquid stream), where the reaction mixture is continuously introduced through the line 16 (reaction mixture feed line) into the evaporator 2.

The evaporation may be performed by reducing the pressure with or without heating. In the evaporation step, the vapor stream temperature is typically 100° C. to 260° C., and preferably 120° C. to 200° C.; the residue stream temperature is typically 80° C. to 200° C., and preferably 100° C. to 180° C.; and the evaporator internal pressure is typically 50 to 1000 kPa (absolute pressure).

The ratio of the vapor stream to the residue stream, which are separated from each other in the evaporation step, is typically from 10:90 to 50:50 in terms of mass ratio. The vapors formed in the step typically include methyl iodide, hydrogen iodide, water, methyl acetate, acetic acid, dimethyl ether, methanol, acetaldehyde, formic acid, and propionic acid, as well as alkyl iodides such as ethyl iodide, propyl iodide, butyl iodide, hexyl iodide, and decyl iodide. The vapors are continuously drawn from within the evaporator 2 to the line 17 (vapor stream discharge line).

Of the vapor stream drawn from within the evaporator 2, a portion is continuously introduced into the condenser 2a; and another portion is continuously introduced through the line 21 into the subsequent (downstream) distillation column 3. The vapor stream has an acetic acid concentration of typically 40 to 85 mass percent (preferably 50 to 85 mass percent), and more preferably 50 to 75 mass percent (e.g., 55 to 75 mass percent); a methyl iodide concentration of typically 2 to 50 mass percent (preferably 5 to 30 mass percent); a water concentration of typically 0.2 to 20 mass percent (and preferably 1 to 15 mass percent); and a methyl acetate concentration of typically 0.2 to 50 mass percent (and preferably 2 to 30 mass percent). The vapor stream has a hexyl iodide concentration of typically 0.1 to 10000 ppb by mass, generally 0.5 to 1000 ppb by mass, and frequently 1 to 100 ppb by mass (e.g., 2 to 50 ppb by mass).

The residue stream formed in the step includes the catalyst and the promoter (such as methyl iodide and/or lithium iodide), which have been contained in the reaction mixture; and water, methyl acetate, acetic acid, formic acid, propionic acid, and other substances that remain without volatilization in the step. The residue stream is continuously introduced from the evaporator 2 through the line 18 into the heat exchanger 2b, using the pump 57. The heat exchanger 2b cools the residue stream from the evaporator 2. The cooled residue stream is continuously introduced and recycled from the heat exchanger 2b through the line 19 to the reactor 1. The line 18 and the line 19 are also collectively referred to as a "residue stream recycle line(s)". The residue stream has an acetic acid concentration of typically 55 to 90 mass percent, and preferably 60 to 85 mass percent.

The condenser 2a cools and partially condenses the vapor stream from the evaporator 2 to separate the vapor stream into a condensate and a gas. The condensate typically includes methyl iodide, hydrogen iodide, water, methyl acetate, acetic acid, dimethyl ether, methanol, acetaldehyde, formic acid, and propionic acid; and is introduced and recycled from the condenser 2a through the lines 22 and 23 to the reactor 1. The gas typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid; and is fed from the condenser 2a through the lines 20 and 15 to the scrubbing system 8. The acetic acid formation reaction in the reaction step is an exothermic reaction. A portion of heat accumulated in the reaction mixture is, in the evaporation step (flash step), transferred to the vapors derived from the reaction mixture. The vapors are cooled in the condenser 2a to give a condensate, and the condensate is recycled to the reactor 1. Specifically, this acetic acid production equipment enables efficient removal of heat by the working of the condenser 2a, where the heat is generated in the methanol-carbonylation reaction.

The distillation column 3 is a unit with which the first distillation step is performed. The distillation column 3 in the embodiment is characterized as a so-called light ends column. The first distillation step is the step of subjecting the vapor stream, which is continuously introduced into the distillation column 3, to distillation treatment to separate and remove one or more light ends therefrom. More specifically, the first distillation step is the step of separating, by distillation, the vapor stream into an overhead stream rich in at least one light end selected from methyl iodide and acetaldehyde, and an acetic acid stream rich in acetic acid.

The distillation column 3 may be selected typically from rectification columns such as a plate column and a packed column. The distillation column 3, when being a plate column, typically has 5 to 50 theoretical plates and is operated at a reflux ratio of typically 0.5 to 3000, where the reflux ratio may be determined according to the number of theoretical plates. In the distillation column 3, the column top pressure is set typically to 80 to 160 kPaG, and the column bottom pressure is set to a pressure higher than the column top pressure and is typically 85 to 180 kPaG. In the distillation column 3, the column top temperature is set typically to a temperature which is lower than the boiling point of acetic acid at the set column top pressure and is from 90° C. to 130° C.; and the column bottom temperature is set typically to a temperature equal to or higher than the boiling point of acetic acid at the set column bottom pressure and is from 120° C. to 165° C. (preferably from 125° C. to 160° C.)

At the distillation column 3, the vapor stream from the evaporator 2 is continuously introduced through the line 21; vapors as an overhead stream are continuously drawn from a column top portion to the line 24; and bottoms are continuously drawn from a column bottom portion to the line 25. There is disposed the reboiler 3b. An acetic acid stream (first acetic acid stream; liquid) as a side stream is continuously drawn, through the line 27, from a portion at a height position between the column top and the column bottom in the distillation column 3.

The vapors drawn from the column top portion of the distillation column 3 include light ends in larger amounts as compared with the bottoms and the side stream from the distillation column 3, where the light ends are components having lower boiling points as compared with acetic acid. The vapors typically include methyl iodide, hydrogen iodide, water, methyl acetate, dimethyl ether, methanol, acetaldehyde, and formic acid. The vapors also include acetic acid. The vapors as above are continuously introduced through the line 24 into the condenser 3a.

The condenser 3a cools and partially condenses the vapors from the distillation column 3 to separate the vapors into a condensate and a gas. The condensate typically includes methyl iodide, hydrogen iodide, water, methyl acetate, acetic acid, dimethyl ether, methanol, acetaldehyde, and formic acid. The condensate is continuously introduced from the condenser 3a through the line 28 into the decanter 4. The condensate introduced into the decanter 4 is liquid-liquid separated into an aqueous phase (upper phase) and an organic phase (methyl iodide phase; lower phase).

The aqueous phase includes water, and other components such as methyl iodide, hydrogen iodide, methyl acetate, acetic acid, dimethyl ether, methanol, acetaldehyde, and formic acid. The organic phase typically includes methyl iodide, and other components such as hydrogen iodide, water, methyl acetate, acetic acid, dimethyl ether, methanol, acetaldehyde, and formic acid.

In the embodiment, of the aqueous phase, a portion is refluxed through the line 29 to the distillation column 3; and another portion is introduced and recycled through the lines 29, 30, and 23 to the reactor 1. A portion of the organic phase is introduced and recycled through the lines 31 and 23 to the reactor 1. Another portion of the organic phase and/or another portion of the aqueous phase is introduced through the lines 31 and 50 and/or through the lines 30 and 51 into the acetaldehyde-removing system 9. To the aqueous phase in the decanter 4, the first or second solution containing water may be recycled. The water in the first or second solution is merged with the aqueous phase and is treated together with the aqueous phase.

In an acetaldehyde-removing step using the acetaldehyde-removing system 9, acetaldehyde is removed from at least one of the organic phase and the aqueous phase by a known technique such as distillation, or extraction, or both in combination. The separated acetaldehyde is discharged through the line 53 out of the equipment. Useful components (such as methyl iodide) contained in at least one of the organic phase and the aqueous phase are recycled through the lines 52 and 23 to the reactor 1.

FIG. 7 depicts a schematic flow chart illustrating an acetaldehyde-removing system according to an embodiment. For example, assume that the organic phase is treated in the acetaldehyde-removing step according to the flow. In this case, the organic phase is treated typically by a procedure as follows. The organic phase is fed through a line 101 to a distillation column (first acetaldehyde-removing column) 91 and is separated by distillation into an overhead stream rich in acetaldehyde (line 102), and a residue stream rich in methyl iodide (residual liquid stream; bottoms stream) (line 103). The overhead stream is condensed in a condenser 91a to give a condensate. Of the condensate, a portion (line 104) is refluxed to a column top portion of the distillation column 91; and the remainder (line 105) is fed to an extraction column 92.

The condensate fed to the extraction column 92 is extracted with water introduced from a line 109, to give an extract. The extract resulting from the extraction is fed through a line 107 to a distillation column (second acetaldehyde-removing column) 93 and is separated by distillation into an overhead stream rich in acetaldehyde (line 112) and a residue stream rich in water (line 113). The overhead stream rich in acetaldehyde is condensed in a condenser 93a to give a condensate. Of the condensate, a portion (line 114) is refluxed to a column top portion of the distillation column 93; and the remainder (line 115) is discharged out of the system.

The residue stream rich in methyl iodide as bottoms from the first acetaldehyde-removing column 91, a raffinate rich in methyl iodide (line 108) from the extraction column 92, and the residue stream rich in water as bottoms from the second acetaldehyde-removing column 93 are recycled respectively through the lines 103, 111, and 113 to the reactor 1, and/or to an appropriate site in the process and reused. For example, the raffinate rich in methyl iodide from the extraction column 92 can be recycled through a line 110 to the distillation column 91. The liquid in the line 113 is generally discharged out as an effluent. Gases (lines 106 and 116), which have not been condensed in the condensers 91a and 93a, are subjected to absorptive treatment in the scrubbing system 8, or discarded.

Also assume that the aqueous phase is treated in the acetaldehyde-removing step according to the flow illustrated in FIG. 7. In this case, the aqueous phase is treated typically by a procedure as follows. The aqueous phase is fed through the line 101 to the distillation column (first acetaldehyde-removing column) 91, and is separated by distillation into an overhead stream rich in acetaldehyde (line 102) and a residue stream rich in water (line 103). The overhead stream is condensed in the condenser 91a to give a condensate. Of the condensate, a portion (line 104) is refluxed to the column top portion of the distillation column 91; and the remainder (line 105) is fed to the extraction column 92.

The condensate fed to the extraction column 92 is extracted with water introduced from the line 109, to give an extract. The extract resulting from the extraction is fed through the line 107 to the distillation column (second acetaldehyde-removing column) 93, and is separated by distillation into an overhead stream rich in acetaldehyde (line 112) and a residue stream rich in water (line 113). The overhead stream rich in acetaldehyde is condensed in the condenser 93a to give a condensate. Of the condensate, a portion (line 114) is refluxed to the column top portion of the distillation column 93; and the remainder (line 115) is discharged out of the system.

The residue stream rich in water as bottoms from the first acetaldehyde-removing column 91, a raffinate rich in methyl iodide (line 108) from the extraction column 92, and the residue stream rich in water as bottoms from the second acetaldehyde-removing column 93 are recycled respectively through the lines 103, 111, and 113 to the reactor 1, and/or to an appropriate site in the process and reused. For example, the raffinate rich in methyl iodide from the extraction column 92 can be recycled through the line 110 to the distillation column 91. The liquid in the line 113 is generally discharged out as an effluent. Gases (lines 106 and 116), which have not been condensed in the condensers 91a and 93a, are subjected to absorptive treatment in the scrubbing system 8, or discarded.

Instead of, or in addition to the technique, acetaldehyde derived from the process stream including water, acetic acid (AC), methyl iodide (MeI), and acetaldehyde (AD) can also be removed by utilizing extractive distillation. For example, acetaldehyde can be discharged out of the system by the following procedure. The process stream is liquid-liquid separated into an organic phase and an aqueous phase, and at least one of the organic phase and the aqueous phase is fed as a charge liquid to a distillation column (extractive distillation column). With this, an extractant (generally, water) is introduced into a concentrated zone in the distillation column, where methyl iodide and acetaldehyde are concentrated in the concentrated zone. A non-limiting example of the concentrated zone is space ranging from the column top to the charge liquid feeding height. A liquid (extract) falling down from the concentrated zone is drawn as a side stream (sidecut stream), the side stream is liquid-liquid separated into an aqueous phase and an organic phase, and the aqueous phase is subjected to distillation. Thus, acetaldehyde is discharged out of the system.

When a relatively large amount of water is present in the distillation column, the liquid falling down from the concentrated zone may be drawn as a side stream without introduction of the extractant to the distillation column. For example, it is acceptable that this distillation column is provided with a unit (such as a chimney tray) capable of receiving the liquid (extract) falling down from the concentrated zone, and the liquid (extract) received by the unit is drawn as a side stream.

The extractant is preferably introduced into the distillation column at a height higher than the charge liquid feeding height and is more preferably introduced into a portion of the distillation column adjacent to the column top. The side stream is preferably drawn from the distillation column at a height lower than the extractant introducing height and higher than the charge liquid feeding height. This technique enables high-concentration extraction of acetaldehyde from the concentrate of methyl iodide and acetaldehyde, with the extractant (generally, water). In addition, the technique enables efficient extraction of acetaldehyde with a small amount of the extractant, because of using, as an extraction zone, space between the extractant introducing height and the sidecut height. The technique can therefore significantly reduce the number of plates in the distillation column and can reduce the required steam amount, as compared typically with a technique of drawing an extract resulting from extractive distillation from a column bottom portion of a distillation column (extractive distillation column). Further, the technique enables removal of acetaldehyde under such conditions as to restrain or minimize the loss of methyl iodide out of the system, because the technique, as using a small amount of the extractant, can reduce the ratio (MeI/AD ratio) of methyl iodide to acetaldehyde in the aqueous extract as compared with the technique illustrated in FIG. 7, which technique employs acetaldehyde removing distillation and aqueous extraction in combination.

The acetaldehyde concentration in the side stream is significantly higher than the acetaldehyde concentrations in the charge liquid and in the bottoms (bottom liquid). The ratio of acetaldehyde to methyl iodide in the side stream is higher than the ratios of acetaldehyde to methyl iodide in the charge liquid and in the bottoms.

An organic phase (methyl iodide phase) resulting from liquid-liquid separation of the side stream may be recycled to this distillation column. In this case, the organic phase resulting from liquid-liquid separation of the side stream is preferably recycled to the distillation column at a height lower than the side stream drawing height and higher than the charge liquid feeding height.

A miscible solvent may be introduced into the distillation column (extractive distillation column), where the miscible solvent is miscible with a component or components (such as methyl acetate) constituting the organic phase resulting from liquid-liquid separation of the process stream. Non-limiting examples of the miscible solvent include acetic acid and ethyl acetate. The miscible solvent is preferably introduced into the distillation column at a height lower than the side stream drawing height and higher than the charge liquid feeding height. When the organic phase resulting from liquid-liquid separation of the side stream is recycled to this distillation column, the miscible solvent is preferably introduced to a portion at a height lower the organic phase recycling height.

Recycling of the organic phase resulting from liquid-liquid separation of the side stream to the distillation column and/or the introduction of the miscible solvent to the distillation column can lower the methyl acetate concentration in the extract drawn as the side stream, can lower the methyl acetate concentration in the aqueous phase resulting from liquid-liquid separation of the extract, and, consequently, can restrain or minimize the contamination of the aqueous phase with methyl iodide.

The distillation column (extractive distillation column) has typically 1 to 100, preferably 2 to 50, furthermore preferably 3 to 30, and particularly preferably 5 to 20 theoretical plates. Thus, the distillation column according to the technique enables efficient separation and removal of acetaldehyde with a smaller number of plates (theoretical plates), as compared with the number of plates (80 to 100 theoretical plates) in distillation columns and extractive distillation columns for use in conventional acetaldehyde removal.

The mass ratio of the extractant flow rate to the charge liquid flow rate may be selected within the range of from 0.0001:100 to 100:100, but is generally from 0.0001:100 to 20:100, preferably from 0.001:100 to 10:100, more preferably from 0.01:100 to 8:100, and furthermore preferably from 0.1:100 to 5:100, where the charge liquid is at least one of the organic phase and the aqueous phase resulting from liquid-liquid separation of the process stream.

At the distillation column (extractive distillation column), the column top temperature is typically 15° C. to 120° C., preferably 20° C. to 90° C., more preferably 20° C. to 80° C., and furthermore preferably 25° C. to 70° C.; and the column top pressure is typically about 0.1 to about 0.5 MPa (absolute pressure). Other conditions for the distillation column (extractive distillation column) may be as with conditions for distillation columns and extractive distillation columns for use in conventional acetaldehyde removal.

FIG. 8 depicts a schematic flow chart illustrating an acetaldehyde-removing system using the extractive distillation, according to an embodiment. In this embodiment, at least one of the organic phase and the aqueous phase resulting from liquid-liquid separation of the process stream is fed as a charge liquid through a feed line 201 to an intermediate plate (at a height between the column top and the column bottom) of a distillation column 94, and water is introduced through a line 202 into a portion adjacent to the column top. Thus, extractive distillation is performed in the distillation column 94 (extractive distillation column).

The distillation column 94 is provided with a chimney tray 200 at a height higher than the charge liquid feeding height, where the chimney tray 200 is capable of receiving a liquid (extract) falling down from a concentrated zone in the column, and where methyl iodide and acetaldehyde are concentrated in the concentrated zone. In this extractive distillation, a liquid on the chimney tray 200 is drawn, preferably in the whole quantity, through a line 208 and introduced into, and liquid-liquid separated in a decanter 95 to give an aqueous phase and an organic phase.

The aqueous phase (including acetaldehyde) is fed from the decanter 95 through a line 212 and introduced into and cooled in a cooler 95*a*. Thus, methyl iodide dissolved in the aqueous phase is two-phase separated, followed by liquid-liquid separation in a decanter 96 to give an aqueous phase and an organic phase. The aqueous phase is fed from the decanter 96 through a line 216 to a distillation column 97 (acetaldehyde-removing column) and undergoes distillation. Vapors from the column top are fed through a line 217 and introduced into and condensed in a condenser 97*a* to give a condensate (mainly including acetaldehyde and methyl iodide). Of the condensate, a portion is refluxed to the column top of the distillation column 97; and the remainder is discarded, or fed through a line 220 to a distillation column 98 (extractive distillation column).

Water is introduced through a line 222 into the distillation column 98 at a portion adjacent to the column top, to perform extractive distillation. Vapors from the column top are brought through a line 223 into, and are condensed in a condenser 98a to give a condensate (mainly including methyl iodide). Of the condensate, a portion is refluxed to the column top portion; and the remainder is recycled through a line 226 to the reaction system, or may be removed (discharged) out of the system. The organic phase (methyl iodide phase) from the decanter 95 is recycled, preferably in the whole quantity, through lines 209 and 210 to the distillation column 94 at a height lower than the height of the chimney tray 200. A portion of the aqueous phase from the decanter 95, and the organic phase from the decanter 96 are recycled respectively through lines 213 and 210 and through lines 214 and 210 to the distillation column 94, but this recycling is not always performed. A portion of the aqueous phase from the decanter 95 may be used as the extractant (water) in the distillation column 94. A portion of the aqueous phase from the decanter 96 may be recycled through the line 210 to the distillation column 94.

In some cases (such as the case where the charge liquid contains methyl acetate), the distillation efficiency can be improved by charging a miscible solvent through a line 215 to the distillation column 94, where the miscible solvent is miscible with a component or components (such as methyl acetate) constituting the organic phase resulting from liquid-liquid separation of the process stream, and the miscible solvent herein is exemplified by acetic acid and ethyl acetate. The miscible solvent is fed to the distillation column 94 at a height higher than the charge liquid feeding height (line 201 coupling height) and lower than the recycle line 210 coupling height. Bottoms from the distillation column 94 are recycled to the reaction system.

Vapors from the column top of the distillation column 94 are fed through a line 203 and brought into and condensed in a condenser 94a to give a condensate, and the condensate is liquid-liquid separated in a decanter 99 into an aqueous phase and an organic phase. The organic phase is refluxed through a line 206 to the column top portion of the distillation column 94, and the aqueous phase is brought through a line 207 to the decanter 95.

Bottoms (mainly containing water) from the distillation column 97 and bottoms (water containing a small amount of acetaldehyde) from the distillation column 98 (extractive distillation column) are transferred respectively through lines 218 and 224 and removed from the system, or recycled to the reaction system. Gases (lines 211, 221, and 227), which have not been condensed in the condensers 94a, 97a, and 98a, are each subjected to absorption treatment in the scrubbing system 8, or discarded.

FIG. 9 depicts a schematic flow chart illustrating an acetaldehyde-removing system using the extractive distillation, according to another embodiment. In this embodiment, the condensate derived from the vapors from the column top of the distillation column 94 is brought into a hold tank 100, and the whole quantity of the condensate is refluxed through a line 206 to a column top portion of the distillation column 94. The other configurations than this are as in the embodiment illustrated in FIG. 8.

FIG. 10 depicts a schematic flow chart illustrating an acetaldehyde-removing system using the extractive distillation, according to yet another embodiment. In this embodiment, the whole quantity of a liquid on the chimney tray 200 is drawn, introduced through the line 208 directly into the cooler 95a without passing through the decanter 95, and cooled in the cooler 95a and fed to the decanter 96. The other configurations than this are as in the embodiment illustrated in FIG. 9.

Referring back to FIG. 6, the gas formed in the condenser 3a typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 3a through the lines 32 and 15 to the scrubbing system 8. Of the gas that reaches the scrubbing system 8, components such as methyl iodide, hydrogen iodide, water, methyl acetate, acetic acid, dimethyl ether, methanol, acetaldehyde, and formic acid are absorbed by the absorbing liquid in the scrubbing system 8. Assume that an absorbing liquid including methanol or methyl acetate is used as the absorbing liquid (absorbent) in the absorption step according to the present invention, the first absorption step, or the second absorption step. In this case, hydrogen iodide reacts with methanol or methyl acetate in the absorbing liquid to form methyl iodide. The resulting liquid (overhead stream from the column top of the distillation column 84) containing the methyl iodide and other useful components can be recycled from the scrubbing system 8 through the recycle lines 48 and 23 to the reactor 1 and reused.

The bottoms drawn from the column bottom portion of the distillation column 3 include larger amounts of heavy ends as compared with the overhead stream and the side stream from the distillation column 3, and typically include propionic acid, as well as the catalyst and the promoter as being entrained, where heavy ends are components having higher boiling points as compared with acetic acid. The bottoms also include other components such as acetic acid, methyl iodide, methyl acetate, and water. In the embodiment, of the bottoms as above, a portion is continuously introduced and recycled through the lines 25 and 26 to the evaporator 2; and another portion is continuously introduced and recycled through the lines 25 and 23 to the reactor 1.

The first acetic acid stream, which is continuously drawn as a side stream from the distillation column 3, is enriched with acetic acid as compared with the vapor stream, which is continuously introduced into the distillation column 3. Namely, the acetic acid concentration in the first acetic acid stream is higher than the acetic acid concentration in the vapor stream. The acetic acid concentration in the first acetic acid stream is typically 90 to 99.9 mass percent, and preferably 93 to 99 mass percent. In addition to acetic acid, the first acetic acid stream further includes other components such as methyl iodide, hydrogen iodide, water, methyl acetate, dimethyl ether, methanol, acetaldehyde, formic acid, and propionic acid, as well as alkyl iodides such as ethyl iodide, propyl iodide, butyl iodide, hexyl iodide, and decyl iodide.

The line 27 may be coupled to the distillation column 3 at a height higher than the coupling height of the line 21 to the distillation column 3 as illustrated in the figure, but may also be coupled at a height lower than or equal to, the coupling height of the line 21 to the distillation column 3. The first acetic acid stream from the distillation column 3 is introduced through the line 27 into the subsequent (downstream) distillation column 5 continuously at a predetermined flow rate. It is also acceptable that the first acetic acid stream drawn as a side stream from the distillation column 3, the bottoms from the distillation column 3, and/or a condensate of vapors in the column bottom portion of the distillation column 3 is continuously introduced into the after-mentioned distillation column 6 without passing through the distillation column 5 (dehydration step).

To the first acetic acid stream flowing through the line 27, potassium hydroxide may be fed or added through the line 55 (potassium hydroxide inlet line). The potassium hydroxide may be fed or added typically as a solution such as an aqueous solution. The feeding or addition of potassium hydroxide to the first acetic acid stream can decrease hydrogen iodide in the first acetic acid stream. Specifically, hydrogen iodide reacts with potassium hydroxide to give potassium iodide and water. This can decrease hydrogen iodide-induced corrosion of the equipment such as distillation columns. In this process, potassium hydroxide can be fed or added to an appropriate site where hydrogen iodide is present. The potassium hydroxide added in the process also reacts with acetic acid to give potassium acetate.

The distillation column 5 is a unit with which the second distillation step is performed. The distillation column 5 in the embodiment is characterized as a so-called dehydration column. The second distillation step is the step of subjecting the first acetic acid stream, which is continuously introduced into the distillation column 5, to distillation treatment to further purify acetic acid.

The distillation column 5 is selected typically from rectification columns such as a plate column and a packed column. The distillation column 5, when being a plate column, typically has 5 to 50 theoretical plates and is operated at a reflux ratio of typically 0.2 to 3000, where the reflux ratio may be determined according to the number of theoretical plates. In the distillation column 5 during the second distillation step, the column top pressure is set typically to 150 to 250 kPaG; and the column bottom pressure is set typically to a pressure which is higher than the column top pressure and is typically 160 to 290 kPaG. In the distillation column 5 during the second distillation step, the column top temperature is set typically to a temperature which is higher than the boiling point of water and lower than the boiling point of acetic acid at the set column top pressure and is from 130° C. to 160° C.; and the column bottom temperature is typically set to a temperature which is equal to or higher than the boiling point of acetic acid at the set column bottom pressure and is from 150° C. to 175° C.

At the distillation column 5, vapors as an overhead stream are continuously drawn from a column top portion to the line 33; and bottoms are continuously drawn from a column bottom portion to the line 34. There is disposed the reboiler 5b. A side stream (liquid or gas) may be continuously drawn to the line 34 from the distillation column 5 at a height position between the column top and the column bottom.

The vapors drawn from the column top portion of the distillation column 5 include larger amounts of light ends as compared with the bottoms from the distillation column 5 and typically include methyl iodide, hydrogen iodide, water, methyl acetate, acetic acid, dimethyl ether, methanol, acetaldehyde, and formic acid, where the light ends are components having lower boiling points as compared with acetic acid. The vapors as above are continuously introduced through the line 33 into the condenser 5a.

The condenser 5a cools and partially condenses the vapors from the distillation column 5 to separate the vapors into a condensate and a gas. The condensate typically includes water and acetic acid. Of the condensate, a portion is continuously refluxed from the condenser 5a through the line 35 to the distillation column 5; and another portion is continuously introduced and recycled from the condenser 5a through the lines 35, 36, and 23 to the reactor 1. The gas from the condenser 5a typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 5a through the lines 37 and 15 to the scrubbing system 8. The gas from the condenser 5a may be fed to the scrubbing system 8 without being merged into the line 15, as described above. Hydrogen iodide in the gas that reaches the scrubbing system 8 is absorbed by the absorbing liquid in the scrubbing system 8, and then reacts with methanol or methyl acetate in the absorbing liquid, to give methyl iodide. The resulting liquid (overhead stream from the column top of the distillation column 84) containing the methyl iodide and other useful components is recycled from the scrubbing system 8 through the recycle lines 48 and 23 to the reactor 1 and reused.

The bottoms drawn from the column bottom portion of the distillation column 5 (or the side stream) include larger amounts of heavy ends as compared with the overhead stream from the distillation column 5, where the heavy ends are components having higher boiling points as compared with acetic acid. The bottoms (or the side stream) typically include acetic anhydride, propionic acid, acetate salts, and iodide salts such as potassium iodide and metal iodides derived from metals such as corrosion metals, as well as the catalyst and the promoter as being entrained. Non-limiting examples of the acetate salts include metal acetates such as potassium acetate which is formed when potassium hydroxide or another alkali is fed typically to the line 27. Non-limiting examples of the acetate salts also include metal acetates formed by acetic acid and metals such as corrosion metals, including metals liberated from the inner walls of constitutional elements of the acetic acid production equipment. A non-limiting example of the iodide salts is potassium iodide which is formed when potassium hydroxide or another alkali is fed typically to the line 27. The bottoms may also include acetic acid. The bottoms as above are continuously introduced, as a second acetic acid stream, through the line 34 into the subsequent (downstream) distillation column 6. The bottoms drawn from the column bottom portion of the distillation column 5 (or side stream) also include the metals such as corrosion metals; and compounds (iodide salts) between the metals such as corrosion metals and iodine derived from corrosive iodine. The bottoms as above are, in the embodiment, discharged out of the acetic acid production equipment.

The second acetic acid stream is enriched with acetic acid as compared with the first acetic acid stream, which is continuously introduced into the distillation column 5. Specifically, the acetic acid concentration in the second acetic acid stream is higher than the acetic acid concentration in the first acetic acid stream. The acetic acid concentration in the second acetic acid stream is typically 99.1 to 99.99 mass percent, as long as being higher than the acetic acid concentration in the first acetic acid stream. The second acetic acid stream may include other components such as propionic acid and hydrogen iodide in addition to acetic acid, as described above. In the embodiment, the side stream, when to be drawn, is drawn from the distillation column 5 at a height lower than the height at which the first acetic acid stream is introduced into the distillation column 5.

To the second acetic acid stream flowing through the line 34, potassium hydroxide may be fed or added through the line 56 (potassium hydroxide inlet line). The potassium hydroxide may be fed or added as a solution such as an aqueous solution. The feeding or addition of potassium hydroxide to the second acetic acid stream can decrease hydrogen iodide in the second acetic acid stream. Specifically, hydrogen iodide reacts with potassium hydroxide to form potassium iodide and water. This can decrease corrosion of the equipment such as distillation columns, where the corrosion will be caused by hydrogen iodide.

The distillation column 6 is a unit with which the third distillation step is performed. The distillation column 6 in the embodiment is characterized as a so-called heavy ends column. The third distillation step is the step of subjecting the second acetic acid stream, which is continuously introduced into the distillation column 6, to purification treatment to further purify acetic acid.

The distillation column 6 may be selected typically from rectification columns such as a plate column and a packed column. The distillation column 6, when being a plate column, typically has 5 to 50 theoretical plates and is operated at a reflux ratio of typically 0.2 to 3000, where the reflux ratio may be determined according to the number of theoretical plates. In the distillation column 6 during the third distillation step, the column top pressure is set typically to −100 to 150 kPaG; and the column bottom pressure is set to a pressure which is higher than the column top pressure and is typically −90 to 180 kPaG. In the distillation column 6 during the third distillation step, the column top temperature is set typically to a temperature which is higher than the boiling point of water and lower than the boiling point of acetic acid at the set column Lop pressure and is from 50° C. to 150° C.; and the column bottom temperature is set typically to a temperature which is higher than the boiling point of acetic acid at the set column bottom pressure and is from 70° C. to 160° C.

At the distillation column 6, vapors as an overhead stream are continuously drawn from a column top portion to the line 38; and bottoms are continuously drawn from a column bottom portion to the line 39. There is disposed the reboiler 6b. A side stream (liquid or gas) is continuously drawn, to the line 46, from the distillation column 6 at a height position between the column top and the column bottom. The line 46 may be coupled to the distillation column 6 at a height higher than the coupling height of the line 34 to the distillation column 6, as illustrated in the figure, but may be coupled at a height lower than or equal to, the coupling height of the line 34 to the distillation column 6.

The vapors drawn from the column top portion of the distillation column 6 include larger amounts of light ends as compared with the bottoms from the distillation column 6, where the light ends are components having lower boiling points as compared with acetic acid. The vapors include acetic acid; and other components such as methyl iodide, hydrogen iodide, water, methyl acetate, dimethyl ether, methanol, and formic acid. The vapors as above are continuously introduced through the line 38 into the condenser 6a.

The condenser 6a cools and partially condenses the vapors from the distillation column 6 to separate the vapors into a condensate and a gases. The condensate includes acetic acid; and other components such as methyl iodide, hydrogen iodide, water, methyl acetate, dimethyl ether, methanol, and formic acid. At least a portion of the condensate is continuously refluxed from the condenser 6a through the line 40 to the distillation column 6. A portion (distillate) of the condensate can be recycled from the condenser 6a through the lines 40, 41, and 42 to the first acetic acid stream in the line 27 before introduction into the distillation column 5. In addition to or instead of this, a portion (distillate) of the condensate can be recycled from the condenser 6a through the lines 40, 41, and 43 to the vapor stream in the line 21 before introduction into the distillation column 3.

A portion (distillate) of the condensate may be recycled from the condenser 6a through the lines 40, 44, and 23 to the reactor 1. A portion of the distillate from the condenser 6a can be fed to the scrubbing system 8 and be used as the absorbing liquid in the system, as described above. At the scrubbing system 8, gases from which useful components have been absorptively removed are discharged out of the equipment, whereas the liquid (overhead stream from the column top of the distillation column 84) containing the useful components is introduced or recycled from the scrubbing system 8 through the recycle lines 48 and 23 to the reactor 1 and reused. In addition, a portion of the distillate from the condenser 6a may be brought through lines (not shown) to various pumps (not shown) operated in the equipment and be used as a sealing liquid for the pumps. Further, a portion of the distillate from the condenser 6a may be drawn out of the system through a draw line attached to the line 40 steadily, or non-steadily at the time of need.

When a portion (distillate) of the condensate is removed from the distillation treatment system in the distillation column 6, the amount of the distillate (distillate amount) is typically 0.01 to 30 mass percent, preferably 0.1 to 10 mass percent, more preferably 0.3 to 5 mass percent, and furthermore preferably 0.5 to 3 mass percent, of the condensate obtained by the working of the condenser 6a. In contrast, the gas formed in the condenser 6a typically includes carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid. The gas is fed from the condenser 6a through the lines 45 and 15 to the scrubbing system 8. The gas from the condenser 6a may be fed to the scrubbing system 8 without being merged into the line 15, as described above.

The bottoms drawn from the column bottom portion of the distillation column 6 through the line 39 include larger amounts of heavy ends as compared with the overhead stream from the distillation column 6 and typically include acetate salts, acetic anhydride, and propionic acid, where the heavy ends are components having higher boiling points as compared with acetic acid. A non-limiting example of the acetate salts is potassium acetate formed when potassium hydroxide or another alkali is fed typically to the line 34. Non-limiting examples of the acetates also include metal acetates formed between acetic acid and metals such as corrosion metals, which are exemplified by metals liberated from the inner walls of constitutional elements of the acetic acid production equipment. The bottoms drawn from the column bottom portion of the distillation column 6 through the line 39 further include the metals such as corrosion metals; and compounds between the metals such as corrosion metals and iodine derived from corrosive iodine. In the embodiment, the bottoms as above are discharged out of the acetic acid production equipment.

The side stream continuously drawn from the distillation column 6 to the line 46 is continuously introduced, as a third acetic acid stream, into the subsequent (downstream) ion exchange resin column 7. The third acetic acid stream is enriched with acetic acid as compared with the second acetic acid stream, which is continuously introduced into the distillation column 6. Specifically, the acetic acid concentration in the third acetic acid stream is higher than the acetic acid concentration in the second acetic acid stream. The acetic acid concentration in the third acetic acid stream is typically 99.8 to 99.999 mass percent, as long as being higher than the acetic acid concentration in the second acetic acid stream. In the embodiment, the side stream is drawn from the distillation column 6 at a height higher than the height at which the second acetic acid stream is introduced into the distillation column 6. In another embodiment, the side stream is drawn from the distillation column 6 at a height equal to or lower than the height at which the second acetic acid stream is introduced into the distillation column 6. In place of the distillation column 6, a simple distillator (evaporator) is usable. The distillation column 6 can be omitted when impurities are sufficiently removed by the working of the distillation column 5.

The ion exchange resin column 7 is a purification unit with which the adsorptive removing step is performed. The adsorptive removing step is the step of removing, by adsorption, mainly alkyl iodides contained in trace amounts in the third acetic acid stream, to further purify acetic acid, where the third acetic acid stream is continuously introduced into the ion exchange resin column 7. Non-limiting examples of the alkyl iodides include ethyl iodide, propyl iodide, butyl iodide, hexyl iodide, and decyl iodide.

In the ion exchange resin column 7, an ion exchange resin capable of adsorbing alkyl iodides is packed to form an ion exchange resin bed. Non-limiting examples of the ion exchange resin as above include cation-exchange resins with part of leaving protons in exchange groups being substituted or replaced with a metal such as silver or copper, where the exchange groups are exemplified typically by sulfonic groups, carboxy groups, and phosphonate groups. In the adsorptive removing step, the third acetic acid stream (liquid) passes through the inside of the ion exchange resin column 7 packed typically with the ion exchange resin as above, and, during the passing process, alkyl iodides and other impurities are adsorbed and removed from the third acetic acid stream by the ion exchange resin. In the ion exchange resin column 7 during the adsorptive removing step, the internal temperature is typically 18° C. to 100° C., and the acetic acid stream flow rate is typically 3 to 15 $m^3/h \cdot m^3$ (resin volume), where the acetic acid stream flow rate is the acetic acid throughput ($m^3/h$) per cubic meter of the resin volume.

From a bottom portion of the ion exchange resin column 7, a fourth acetic acid stream is continuously drawn to the line 47. The fourth acetic acid stream has a higher acetic acid concentration as compared with the third acetic acid stream. Specifically, the fourth acetic acid stream is enriched with acetic acid as compared with the third acetic acid stream, which is continuously introduced into the ion exchange resin column 7. The acetic acid concentration in the fourth acetic acid stream is typically 99.9 to 99.999 mass percent, or more, as long as being higher than the acetic acid concentration in the third acetic acid stream. In the production method, the fourth acetic acid stream can be stored in a product tank (not shown).

This acetic acid production equipment may include a so-called product column or finishing column as a purification unit for further purifying the fourth acetic acid stream from the ion exchange resin column 7, where the product column or finishing column is a distillation column. The product column as above, when provided, may be selected typically from rectification columns such as a plate column and a packed column. The product column, when being a plate column, typically has 5 to 50 theoretical plates and is operated at a reflux ratio of typically 0.5 to 3000, where the reflux ratio may be determined according to the number of theoretical plates. In the product column during the purification step, the column top pressure is set typically to −195 to 150 kPaG; and the column bottom pressure is set to a pressure which is higher than the column top pressure and is typically −190 to 180 kPaG. In the product column, the column top temperature is typically set to a temperature which is higher than the boiling point of water and lower than the boiling point of acetic acid at the set column top pressure and is from 50° C. to 150° C.; and the column bottom temperature is set typically to a temperature which is higher than the boiling point of acetic acid at the set column bottom pressure and is from 70° C. to 160° C. In place of the product column or finishing column, a simple distillator (evaporator) is usable.

Into the product column, when provided, all or a portion of the fourth acetic acid stream (liquid) from the ion exchange resin column 7 is continuously introduced. At the product column as above, vapors as an overhead stream are continuously drawn from a column top portion, where the vapors include trace amounts of light ends such as methyl iodide, water, methyl acetate, dimethyl ether, crotonaldehyde, acetaldehyde, and formic acid. The vapors are separated, using a predetermined condenser, into a condensate and a gas.

Of the condensates, a portion is continuously refluxed to the product column; and another portion may be recycled to the reactor 1, or be discarded out of the system, or both. The gas is fed to the scrubbing system 8. At the product column, bottoms including trace amounts of heavy ends are continuously drawn from a column bottom portion, and are typically recycled to the second acetic acid stream in the line 34 before introduction into the distillation column 6. At the product column, a side stream (liquid) as a fifth acetic acid stream is continuously drawn from a portion at a height position between the column top and the column bottom. The side stream is drawn from the product column typically at a height lower than the height at which the fourth acetic acid stream is introduced into the product column.

The fifth acetic acid stream is enriched with acetic acid as compared with the fourth acetic acid stream, which is continuously introduced into the product column. Specifically, the acetic acid concentration in the fifth acetic acid stream is higher than the acetic acid concentration in the fourth acetic acid stream. The acetic acid concentration in the fifth acetic acid stream is typically 99.9 to 99.999 mass percent, or more, as long as being higher than the acetic acid concentration in the fourth acetic acid stream. The fifth acetic acid stream is stored typically in a product tank (not shown). Instead of, or in addition to being disposed downstream from the distillation column 6, the ion exchange resin column 7 may be disposed downstream from the product column, for the treatment of the acetic acid stream from the product column.

EXAMPLES

The present invention will be illustrated in further detail with reference to several examples below. It should be noted, however, that the examples are by no means intended to limit the scope of the present invention. All percentages, parts per million (ppm), and parts per billion (ppb) are by mass. Hydrogen iodide concentrations were determined by the subtraction technique.

Comparative Example 1

An experiment was performed using the scrubbing system illustrated in FIG. 11. A high-pressure charge gas (1) and a low-pressure charge gas (5) were charged respectively into a high-pressure absorption column A (having 5 theoretical plates) and a low-pressure absorption column B (having 5 theoretical plates), circulating acetic acid as an absorbent was introduced through the column tops of the two absorption columns, and dispersed from the upper portions of the absorption columns using dispersing plates to absorb condensable gases including an iodine compound or compounds. Thus, an absorption step was performed, and absorbing liquids were drawn from the column bottoms of the absorption columns. A high-pressure offgas (3) from the column top of the high-pressure absorption column A, and a low-pressure offgas (7) from the column top of the low-pressure absorption column B were merged with each other and discharged out of the system. Bottoms (4) from the high-pressure absorption column A and bottoms (8) from the low-pressure absorption column B were merged to give a charge liquid (9). The charge liquid (9) was charged to a central portion (between upper 2.5 theoretical plates and lower 2.5 theoretical plates) of a distillation column C (having 5 theoretical plates) to perform a stripping step. The charge liquid (9) was then heated with steam in the distillation column C, by which light ends other than acetic acid were concentrated at the column top to give an overhead stream (10), and this was distilled at a reflux ratio of 1 and recycled to the reactor, where the reflux ratio was defined as the ratio of the reflux amount to the distillate amount. The amount of steam used herein was defined as 100. Acetic acid (11) after the stripping was drawn from the column bottom of the distillation column C, cooled, combined with fresh acetic acid (12), and cycled as the absorbing liquids (absorbents) (2) and (6) to the high-pressure absorption column and the low-pressure absorption column. The two absorption columns and the distillation column were each packed with a structured packing Mellapak 250X supplied by Sulzer Chemtech Ltd. In this experiment, drawing of the bottoms from the distillation column out of the system was not performed. The distillation column C was operated at a column bottom temperature of 147° C. The flow rates of, and the concentrations of individual components in, the elements (1) to (11) are presented in Table 1.

In the table, "AD" stands for acetaldehyde, "MeI" stands for methyl iodide, "MA" stands for methyl acetate, "AC" stands for acetic acid, and "PA" stands for propionic acid. The symbol "–" in the table indicates that no measurement was performed for the concentration of the component in question. The components "Others" may include, for example, components in the tables whose concentrations had not been measured; methanol, dimethyl ether, alkanes, crotonaldehyde, and other substances that adversely affect the potassium permanganate test result (permanganate time); and organic iodine compounds.

TABLE 1

|  |  | (1) High-pressure charge gas | (2) High-pressure absorption column absorbing liquid | (3) High-pressure offgas | (4) High-pressure absorption column bottoms | (5) Low-pressure charge gas | (6) Low-pressure absorption column absorbing liquid |
|---|---|---|---|---|---|---|---|
| Flow rate | part by mass | 1.2 | 18.6 | 0.9 | 18.9 | 16.0 | 74.5 |
| $H_2$ | mass % | 0.3 | — | 0.4 | — | 0.5 | — |
| CO | mass % | 67.2 | — | 86.3 | — | 42.0 | — |
| $CO_2$ | mass % | 0.9 | — | 1.2 | — | 4.7 | — |
| $CH_4$ | mass % | 3.0 | — | 3.9 | — | 5.3 | — |
| $N_2$ | mass % | 4.8 | — | 6.1 | — | 5.6 | — |
| AD | mass % | 0.3 | — | — | 0.0 | 0.1 | — |
| MeI | mass % | 21.4 | 0.0 | — | 1.4 | 37.1 | 0.0 |
| MA | mass % | — | — | — | — | 1.9 | — |
| $H_2O$ | mass % | 0.0 | 0.3 | — | 0.3 | 0.1 | 0.3 |
| AC | mass % | 0.0 | 99.0 | — | 97.6 | 0.4 | 99.0 |
| PA | mass % | 0.0 | 0.0 | 0.0 | 0.0 | 0.0 | 0.0 |
| HI | mass % | 0.0111 | 0.0014 | 0.0029 | 0.0020 | 0.0083 | 0.0014 |
| Others | mass % | 2.0 | 0.8 | 2.1 | 0.8 | 2.1 | 0.8 |
| Total | mass % | 100.0 | 100.0 | 100.0 | 100.0 | 100.0 | 100.0 |
| Temperature | ° C. | 26.0 | 28.8 | 35.9 | 33.2 | 14.8 | 23.5 |
| Pressure | kPaG | 2760 | 2800 | 2750 | 2750 | 128 | 122 |

|  |  | (7) Low-pressure offgas | (8) Low-pressure absorption column bottoms | (9) Distillation column charge liquid | (10) Distillation column distillate | (11) Distillation column bottoms |
|---|---|---|---|---|---|---|
| Flow rate |  | 9.5 | 81.1 | 100.0 | 11.1 | 88.9 |
| $H_2$ |  | 0.8 | 0.0 | 0.0 | 0.0 | — |
| CO |  | 71.2 | 0.0 | 0.0 | 0.0 | — |
| $CO_2$ |  | 8.0 | 0.0 | 0.0 | 0.0 | — |
| $CH_4$ |  | 9.0 | 0.0 | 0.0 | 0.0 | — |
| $N_2$ |  | 9.6 | 0.0 | 0.0 | 0.0 | — |
| AD |  | — | 0.0 | 0.0 | 0.2 | — |
| MeI |  | — | 7.3 | 6.2 | 55.7 | — |
| MA |  | — | 0.4 | 0.3 | 2.8 | — |
| $H_2O$ |  | — | 0.3 | 0.3 | 0.2 | 0.3 |
| AC |  | — | 91.0 | 92.3 | 38.8 | 99.0 |
| PA |  | 0.0 | 0.0 | 0.0 | 0.0 | 0.0 |
| HI |  | 0.0028 | 0.0026 | 0.0025 | 0.0106 | 0.0015 |
| Others |  | 1.4 | 1.0 | 0.9 | 2.3 | 0.8 |
| Total |  | 100.0 | 100.0 | 100.0 | 100.0 | 100.0 |
| Temperature |  | 24.0 | 32.4 | 24.0 | 24.5 | 146.6 |
| Pressure |  | 122 | 123 | 122 | 119 | 133 |

Comparative Example 2

An experiment was performed by a procedure similar to that in Comparative Example 1, except for not preforming the absorption step using the high-pressure absorption column A. The amount of steam used in the distillation column in the stripping step was 90. The flow rates and the concentrations of individual components in the elements (5) to (11) are given in Table 2.

TABLE 2

|  |  | (5) Low-pressure charge gas | (6) Low-pressure absorption column absorbing liquid | (7) Low-pressure offgas | (8) Low-pressure absorption column bottoms | 9) Distillation column charge liquid | (10) Distillation column distillate | (11) Distillation column bottoms |
|---|---|---|---|---|---|---|---|---|
| Flow rate | part by mass | 16.1 | 74.7 | 9.5 | 81.3 | 100.0 | 10.9 | 89.1 |
| $H_2$ | mass % | 0.5 | — | 0.8 | 0.0 | 0.0 | 0.0 | — |
| CO | mass % | 42.0 | — | 71.2 | 0.0 | 0.0 | 0.0 | — |
| $CO_2$ | mass % | 4.7 | — | 8.0 | 0.0 | 0.0 | 0.0 | — |
| $CH_4$ | mass % | 5.3 | — | 9.0 | 0.0 | 0.0 | 0.0 | — |
| $N_2$ | mass % | 5.6 | — | 9.6 | 0.0 | 0.0 | 0.0 | — |
| AD | mass % | 0.1 | — | — | 0.0 | 0.0 | 0.2 | — |
| MeI | mass % | 37.1 | 0.0 | — | 7.3 | 6.0 | 54.7 | — |
| MA | mass % | 1.9 | — | — | 0.4 | 0.3 | 2.8 | — |
| $H_2O$ | mass % | 0.1 | 0.3 | — | 0.3 | 0.3 | 0.2 | 0.3 |
| AC | mass % | 0.4 | 99.0 | — | 91.0 | 92.5 | 39.7 | 99.0 |
| PA | mass % | 0.0 | 0.0 | 0.0 | 0.0 | 0.0 | 0.0 | 0.0 |
| HI | mass % | 0.0083 | 0.0014 | 0.0028 | 0.0026 | 0.0024 | 0.0098 | 0.0015 |
| Others | mass % | 2.1 | 0.8 | 1.4 | 1.0 | 0.9 | 2.3 | 0.8 |
| Total | mass % | 100.0 | 100.0 | 100.0 | 100.0 | 100.0 | 100.0 | 100.0 |
| Temperature | ° C. | 14.8 | 23.5 | 24.0 | 32.4 | 24.0 | 24.8 | 146.6 |
| Pressure | kPaG | 128 | 122 | 122 | 123 | 122 | 119 | 133 |

Example 1

An experiment was performed by a procedure similar to that in Comparative Example 1, except for using circulating propionic acid as the absorbent to be introduced through the column tops of the high-pressure absorption column A and the low-pressure absorption column B; distilling the whole quantity from the distillation column C out of the system without refluxing; and not supplying the fresh absorbent through the line (12). The amount of steam used in the distillation column in the stripping step was 53, saving the amount of steam by 47% as compared with Comparative Example 1. As a result, the overhead stream (10) from the distillation column C included little propionic acid, and this demonstrated that methyl iodide can be sufficiently separated even under the steam-saving conditions without refluxing. The flow rates and the concentrations of individual components in the elements (1) to (11) are given in Table 3.

TABLE 3

|  |  | (1) High-pressure charge gas | (2) High-pressure absorption column absorbing liquid | (3) High-pressure offgas | (4) High-pressure absorption column bottoms | (5) Low-pressure charge gas | (6) Low-pressure absorption column absorbing liquid |
|---|---|---|---|---|---|---|---|
| Flow rate | part by mass | 1.3 | 18.5 | 1.0 | 18.8 | 16.8 | 74.2 |
| $H_2$ | mass % | 0.3 | — | 0.4 | — | 0.5 | — |
| CO | mass % | 65.7 | — | 86.2 | — | 41.7 | — |
| $CO_2$ | mass % | 0.9 | — | 1.2 | — | 4.7 | — |
| $CH_4$ | mass % | 3.0 | — | 3.9 | — | 5.2 | — |
| $N_2$ | mass % | 4.7 | — | 6.1 | — | 5.6 | — |
| AD | mass % | 0.3 | — |  | 0.0 | 0.1 | — |
| MeI | mass % | 22.3 | — |  | 1.5 | 37.6 | — |
| MA | mass % | — | — | — | — | 1.9 | — |
| $H_2O$ | mass % | 0.1 | 0.3 | — | 0.3 | 0.1 | 0.3 |
| AC | mass % | 0.3 | 0.1 | — | 0.1 | 0.4 | 0.1 |
| PA | mass % | 0.5 | 98.9 | 0.0 | 97.3 | 0.0 | 98.9 |

TABLE 3-continued

| | | | | | | | |
|---|---|---|---|---|---|---|---|
| HI | mass % | 0.0136 | 0.0015 | 0.0029 | 0.0022 | 0.0103 | 0.0015 |
| Others | mass % | 2.0 | 0.7 | 2.1 | 0.8 | 2.1 | 0.7 |
| Total | mass % | 100.0 | 100.0 | 100.0 | 100.0 | 100.0 | 100.0 |
| Temperature | °C. | 26.4 | 30.0 | 35.7 | 33.5 | 14.9 | 23.8 |
| Pressure | kPaG | 2750 | 2800 | 2750 | 2750 | 128 | 123 |

| | (7) Low-pressure offgas | (8) Low-pressure absorption column bottoms | (9) Distillation column charge liquid | (10) Distillation column distillate | (11) Distillation column bottoms |
|---|---|---|---|---|---|
| Flow rate | 9.8 | 81.2 | 100.0 | 7.3 | 92.7 |
| $H_2$ | 0.8 | 0.0 | 0.0 | 0.0 | — |
| CO | 71.2 | 0.0 | 0.0 | 0.0 | — |
| $CO_2$ | 8.0 | 0.0 | 0.0 | 0.0 | — |
| $CH_4$ | 9.0 | 0.0 | 0.0 | 0.0 | — |
| $N_2$ | 9.6 | 0.0 | 0.0 | 0.0 | — |
| AD | — | 0.0 | 0.0 | 0.4 | — |
| MeI | — | 7.8 | 6.6 | 90.4 | — |
| MA | — | 0.4 | 0.3 | 4.4 | — |
| $H_2O$ | — | 0.3 | 0.3 | 0.3 | 0.3 |
| AC | — | 0.2 | 0.1 | 1.0 | 0.1 |
| PA | 0.0 | 90.4 | 91.7 | 0.6 | 98.9 |
| HI | 0.0028 | 0.0032 | 0.0030 | 0.0220 | 0.0015 |
| Others | 1.4 | 0.9 | 0.9 | 2.9 | 0.7 |
| Total | 100.0 | 100.0 | 100.0 | 100.0 | 100.0 |
| Temperature | 23.9 | 32.5 | 24.2 | 24.3 | 167.8 |
| Pressure | 123 | 124 | 123 | 119 | 133 |

Example 2

An experiment was performed by a procedure similar to that in Comparative Example 2, except for using circulating propionic acid as the absorbent to be introduced through the column top to the low-pressure absorption column B; distilling the whole quantity from the distillation column C out of the system without refluxing; and not supplying the fresh absorbent through the line (12). The amount of steam used in the distillation column in the stripping step was 90% of that in Example 1, saving the amount of steam as compared with Comparative Example 2. As a result, the overhead stream (10) from the distillation column C included little propionic acid, and this demonstrated that methyl iodide can be sufficiently separated even under steam-saving conditions without refluxing. The flow rates and the concentrations of individual components in the elements (5) to (11) are given in Table 4.

TABLE 4

| | | (5) Low-pressure charge gas | (6) Low-pressure absorption column absorbing liquid | (7) Low-pressure offgas | (8) Low-pressure absorption column bottoms | 9) Distillation column charge liquid | (10) Distillation column distillate | (11) Distillation column bottoms |
|---|---|---|---|---|---|---|---|---|
| Flow rate | part by mass | 16.9 | 74.4 | 9.9 | 81.4 | 100.0 | 7.0 | 93.0 |
| $H_2$ | mass % | 0.5 | — | 0.8 | 0.0 | 0.0 | 0.0 | — |
| CO | mass % | 41.7 | — | 71.2 | 0.0 | 0.0 | 0.0 | — |
| $CO_2$ | mass % | 4.7 | — | 8.0 | 0.0 | 0.0 | 0.0 | — |
| $CH_4$ | mass % | 5.2 | — | 9.0 | 0.0 | 0.0 | 0.0 | — |
| $N_2$ | mass % | 5.6 | — | 9.6 | 0.0 | 0.0 | 0.0 | — |
| AD | mass % | 0.1 | — | — | 0.0 | 0.0 | 0.3 | — |
| MeI | mass % | 37.6 | — | — | 7.8 | 6.3 | 90.3 | — |
| MA | mass % | 1.9 | — | — | 0.4 | 0.3 | 4.6 | — |
| $H_2O$ | mass % | 0.1 | — | — | 0.3 | 0.3 | 0.3 | 0.3 |
| AC | mass % | 0.4 | 0.1 | — | 0.2 | 0.1 | 1.0 | 0.1 |
| PA | mass % | 0.0 | 98.9 | 0.0 | 90.4 | 92.0 | 0.5 | 98.9 |
| HI | mass % | 0.0103 | 0.0015 | 0.0028 | 0.0032 | 0.0029 | 0.0208 | 0.0015 |
| Others | mass % | 2.1 | 0.7 | 1.4 | 0.9 | 0.9 | 3.0 | 0.7 |
| Total | mass % | 100.0 | 100.0 | 100.0 | 100.0 | 100.0 | 100.0 | 100.0 |
| Temperature | °C. | 14.9 | 23.8 | 23.9 | 32.5 | 24.2 | 24.7 | 167.8 |
| Pressure | kPaG | 128 | 123 | 123 | 124 | 123 | 119 | 133 |

INDUSTRIAL APPLICABILITY

The acetic acid production methods according to the embodiments of the present invention enable industrial production of acetic acid by the methanol carbonylation process (methanol-acetic acid process).

REFERENCE SIGNS LIST 1 reactor
2 evaporator
3, 5, 6 distillation column
4 decanter
7 ion exchange resin column
8 scrubbing system
9 acetaldehyde-removing system
16 reaction mixture feed line
17 vapor stream discharge line
18, 19 residue stream recycle line
54 carbon monoxide-containing gas inlet line
55, 56 potassium hydroxide inlet line
57 catalyst circulating pump
81, 82, 83 absorption column
84 distillation column (stripper)
91 distillation column (first acetaldehyde-removing column)
92 extraction column
93 distillation column (second acetaldehyde-removing column)
94 distillation column (extractive distillation column)
95 decanter
96 decanter
97 distillation column (acetaldehyde-removing column)
98 distillation column (extractive distillation column)
99 decanter
200 chimney tray

The invention claimed is:

1. A method for producing acetic acid, the method comprising
an absorption step of:
  feeding, to an absorption column, at least a portion of offgases formed in an acetic acid production process;
  bringing the fed offgas into contact with an absorbent in the absorption column to allow the absorbent to absorb an iodine compound from the offgas, the absorbent including an organic acid having a higher boiling point as compared with acetic acid; and
  whereby separating into:
    a gas having a lower iodine compound concentration as compared with the offgas; and
    a solution containing the absorbent and the iodine compound.

2. A method for producing acetic acid, the method comprising:
a carbonylation step of reacting methanol with carbon monoxide in the presence of a catalytic system, acetic acid, methyl acetate, and water in a reactor to form acetic acid, the catalytic system including a metal catalyst and methyl iodide; and
a separation step of separating, using at least one selected from evaporators and distillation columns, a reaction mixture from the carbonylation step into:
  a stream including the metal catalyst;
  an acetic acid stream rich in acetic acid; and
  a stream richer in light ends than the acetic acid stream,
the method optionally further comprising
an acetaldehyde-removing system of separating, by distillation using a distillation column or columns, acetaldehyde from at least a portion of a condensate resulting from condensation of the stream richer in light ends,
the method comprising
an absorption step of:
  feeding, to an absorption column, at least one offgas selected from the group consisting of:
    an offgas from the reactor;
    an offgas from the evaporator or evaporators;
    an offgas from the distillation column or columns in the separation step; and
    an offgas from the distillation column or columns in the acetaldehyde-removing system;
  bringing the fed offgas into contact with an absorbent in the absorption column to allow the absorbent to absorb an iodine compound from the offgas, the absorbent including an organic acid having a higher boiling point as compared with acetic acid; and
  whereby separating into:
    a gas having a lower iodine compound concentration as compared with the offgas; and
    a solution containing the absorbent and the iodine compound.

3. A method for producing acetic acid, the method comprising:
a carbonylation step of reacting methanol with carbon monoxide in the presence of a catalytic system, acetic acid, methyl acetate, and water in a reactor to form acetic acid, the catalytic system including a metal catalyst and methyl iodide;
an evaporation step of separating, using an evaporator, a reaction mixture from the carbonylation step into:
  a vapor stream; and
  a residue stream;
a light ends-removing step of separating, by distillation, the vapor stream into:
  an overhead stream rich in light ends; and
  a first acetic acid stream rich in acetic acid; and
a dehydration step of separating, by distillation, the first acetic acid stream into:
  an overhead stream rich in water; and
  a second acetic acid stream richer in acetic acid than the first acetic acid stream,
the method optionally further comprising at least one of:
  a heavy ends-removing step of separating, by distillation, the second acetic acid stream into:
    a bottom stream rich in heavy ends; and
    a third acetic acid stream richer in acetic acid than the acetic acid stream before being subjected to the distillation; and
  an acetaldehyde-removing system of separating acetaldehyde, using a distillation column or columns, from at least a portion of a condensate resulting from condensation of the overhead stream rich in light ends,
the method comprising
an absorption step of:
  feeding, to an absorption column, at least one offgas selected from the group consisting of:
    an offgas from the reactor;
    an offgas from the evaporator;
    an offgas from a distillation column in the light ends-removing step;

an offgas from a distillation column in the dehydration step;

an offgas from a distillation column in the heavy ends-removing step; and an offgas from the distillation column or columns in the acetaldehyde-removing system;

bringing the fed offgas into contact with an absorbent in the absorption column to allow the absorbent to absorb an iodine compound from the offgas, the absorbent including an organic acid having a higher boiling point as compared with acetic acid; and whereby separating into:

a gas having a lower iodine compound concentration as compared with the offgas; and a solution containing the absorbent and the iodine compound.

4. The method for producing acetic acid according to claim 1, wherein the organic acid in the absorbent is present in a concentration of 10 ppm by mass or more.

5. The method for producing acetic acid according to claim 1, wherein the organic acid is an organic acid having a boiling point of 120° C. to 300° C. at atmospheric pressure.

6. The method for producing acetic acid according to claim 1, wherein the organic acid is propionic acid.

7. The method for producing acetic acid according to claim 1, wherein the method comprises a stripping step of separating, by distillation, the solution containing the absorbent and the iodine compound into:

an overhead stream rich in methyl iodide; and a bottom stream rich in the organic acid.

8. The method for producing acetic acid according to claim 7, wherein the overhead stream rich in methyl iodide is recycled to at least one step selected from the group consisting of:

a reaction step;

an evaporation step; and a distillation step.

9. The method for producing acetic acid according to claim 7, wherein a charge liquid to a distillation column in the stripping step has a methyl iodide concentration of 100 ppm by mass or more.

10. The method for producing acetic acid according to claim 7, wherein a charge liquid to a distillation column in the stripping step has a hydrogen iodide concentration of less than 1 mass percent.

11. The method for producing acetic acid according to claim 7, wherein a distillation column in the stripping step is operated at a reflux ratio of 100 or less.

12. The method for producing acetic acid according to claim 7, wherein the bottom stream rich in the organic acid is recycled to at least one of a reaction step and a distillation step.

13. The method for producing acetic acid according to claim 1, wherein a hydrogen iodide concentration in the solution containing the absorbent and the iodine compound is 0.01 ppm by mass or more.

14. The method for producing acetic acid according to claim 1, wherein a methyl iodide concentration in the solution containing the absorbent and the iodine compound is 1 ppm by mass or more.

15. The method for producing acetic acid according to claim 7, wherein the methyl iodide concentration in the overhead stream from the stripping step is 5 mass percent or more.

16. The method for producing acetic acid according to claim 1, wherein the absorption step comprises an absorption step of bringing a high-pressure gas of the offgas into contact with an absorbent to allow the absorbent to absorb an iodine compound from the high-pressure gas, and thereby separating into a gas having a lower iodine compound concentration as compared with the high-pressure gas, and a solution containing the iodine compound and the absorbent; and another absorption step of bringing a low-pressure gas of the offgas into contact with an absorbent to allow the absorbent to absorb an iodine compound from the low-pressure gas, and whereby separating a gas having a lower iodine compound concentration as compared with the low-pressure gas, and a solution containing the absorbent and the iodine compound.

17. The method for producing acetic acid according to claim 1, wherein the absorption step comprising a first absorption step feeding, to an absorption column, at least a portion of offgases formed in the process, bringing the fed offgas into contact with a first absorbent to allow the first absorbent to absorb an iodine compound from the offgas, and whereby separating a first gas having a lower iodine compound concentration as compared with the offgas, and a first solution containing the iodine compound and the first absorbent; and a second absorption step, in an absorption column, bringing the first gas into contact with a second absorbent being different in composition from the first absorbent, to allow the second absorbent to absorb an iodine compound from the first gas, and whereby separating a second gas having a lower iodine compound concentration as compared with the first gas, and a second solution containing the iodine compound and the second absorbent, and wherein at least one of the first absorbent and the second absorbent includes an organic acid having a higher boiling point as compared with acetic acid.

18. The method for producing acetic acid according to claim 17, wherein the iodine compound to be absorbed in the first absorption step is hydrogen iodide, and the iodine compound to be absorbed in the second absorption step is methyl iodide.

19. The method for producing acetic acid according to claim 17, wherein the first absorbent includes water or a basic aqueous solution and the second absorbent includes the organic acid having a higher boiling point as compared with acetic acid.

20. The method for producing acetic acid according to claim 19, wherein the concentration of water in the first absorbent is 10 ppm by mass or more.

* * * * *